United States Patent
Cunnyngham

(10) Patent No.: US 6,927,326 B1
(45) Date of Patent: Aug. 9, 2005

(54) HYBRID MAIZE PLANT AND SEED 32A85

(75) Inventor: Charles T. Cunnyngham, Tipto, IN (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 432 days.

(21) Appl. No.: 10/271,230

(22) Filed: Oct. 15, 2002

Related U.S. Application Data

(60) Provisional application No. 60/354,060, filed on Jan. 30, 2002.

(51) Int. Cl.[7] ............................. A01H 5/10; A01H 5/00; A01H 1/00; C12N 5/04
(52) U.S. Cl. .................... 800/320.1; 435/412; 435/424; 435/430.1; 800/263; 800/264; 800/265; 800/274; 800/275; 800/298
(58) Field of Search ................................ 435/412, 424, 435/430, 430.1; 800/260, 263–266, 268, 274, 275, 295, 298, 320.1

(56) References Cited

U.S. PATENT DOCUMENTS

| | | | |
|---|---|---|---|
| 5,557,034 A | 9/1996 | Williams et al. | 800/320.1 |
| 5,767,344 A | 6/1998 | Gorman | 800/320.1 |
| 5,917,125 A | 6/1999 | Gorman et al. | 800/320.1 |
| 6,114,612 A | 9/2000 | Colbert | 800/320.1 |
| 6,114,613 A | 9/2000 | Colbert et al. | 800/320.1 |
| 6,133,513 A | 10/2000 | Cunnyngham | 800/320.1 |
| 6,133,514 A | 10/2000 | Colbert et al. | 800/320.1 |
| 6,284,953 B1 | 9/2001 | Colbert | 800/320.1 |
| 6,316,704 B1 | 11/2001 | Colbert et al. | 800/320.1 |
| 6,806,410 B1 * | 10/2004 | Tietz | 800/320.1 |

OTHER PUBLICATIONS

Plant Variety Protection Act, Certificate No. 9200086 for Corn 'PHN18' issued Jun. 30, 1992.
Plant Variety Protection Act, Certificate No. 9700208 for Corn, Field 'PH03D' issued Oct. 27, 2000.
Plant Variety Protection Act, Certificate No. 9900356 for Corn, Field 'PH0WD' issued Nov. 06, 2001.
Plant Variety Protection Act, Certificate No. 9900357 for Corn, Field 'PH3GR' issued Nov. 06, 2001.
Plant Variety Protection Act, Certificate No. 9900358 for Corn, Field 'PH3GK' issued Nov. 06, 2001.
Plant Variety Protection Act, Certificate No. 200000198 for Corn, Field 'PH5D6' issued Nov. 06, 2001.
U.S. Appl. No. 10/271,209, filed Oct. 15, 2002 "Inbred Maize Line PH876".

* cited by examiner

*Primary Examiner*—Ashwin Mehta
(74) *Attorney, Agent, or Firm*—McKee, Voorhees & Sease, P.L.C.

(57) ABSTRACT

According to the invention, there is provided a hybrid maize plant, designated as 32A85, produced by crossing two Pioneer Hi-Bred International, Inc. proprietary inbred maize lines. This invention relates to the hybrid seed 32A85, the hybrid plant produced from the seed, and variants, mutants, and trivial modifications of hybrid 32A85. This invention also relates to methods for producing a maize plant containing in its genetic material one or more transgenes and to the transgenic maize plants produced by that method. This invention further relates to methods for producing maize lines derived from hybrid maize line 32A85 and to the maize lines derived by the use of those methods.

18 Claims, No Drawings

HYBRID MAIZE PLANT AND SEED 32A85

CROSS-REFERENCE TO RELATED APPLICATIONS

This application claims benefit of the priority date of U.S. Patent Application Ser. No. 60/354,060 filed Jan. 30, 2002, which is incorporated herein by reference.

FIELD OF THE INVENTION

This invention is in the field of maize breeding, specifically relating to hybrid maize designated 32A85.

BACKGROUND OF THE INVENTION

Plant Breeding

The goal of plant breeding is to combine in a single variety or hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height is important.

Field crops are bred through techniques that take advantage of the plant's method of pollination. A plant is self-pollinated if pollen from one flower is transferred to the same or another flower of the same plant. A plant is sib pollinated when individuals within the same family or line are used for pollination. A plant is cross-pollinated if the pollen comes from a flower on a different plant from a different family or line. The term "cross pollination" and "out-cross as used herein do not include self pollination or sib pollination.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

Maize (*Zea mays* L.), often referred to as corn in the United States, can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

The development of a hybrid maize variety in a maize plant breeding program involves three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected inbred line with an unrelated inbred line to produce the hybrid progeny (F1). After a sufficient amount of inbreeding successive filial generations will merely serve to increase seed of the developed inbred. Preferably, an inbred line should comprise homozygous alleles at about 95% or more of its loci.

During the inbreeding process in maize, the vigor of the lines decreases. Vigor is restored when two different inbred lines are crossed to produce the hybrid progeny (F1). An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid corn plants can then be generated from this hybrid seed supply.

Large scale commercial maize hybrid production, as it is practiced today, requires the use of some form of male sterility system which controls or inactivates male fertility. A reliable method of controlling male fertility in plants also offers the opportunity for improved plant breeding. This is especially true for development of maize hybrids, which relies upon some sort of male sterility system. There are several ways in which a maize plant can be manipulated so that is male sterile. These include use of manual or mechanical emasculation (or detasseling), cytoplasmic genetic male sterility, nuclear genetic male sterility, gametocides and the like.

Hybrid maize seed is often produced by a male sterility system incorporating manual or mechanical detasseling. Alternate strips of two inbred varieties of maize are planted in a field, and the pollen-bearing tassels are removed from one of the inbreds (female) prior to pollen shed. Providing that there is sufficient isolation from sources of foreign maize pollen, the ears of the detasseled inbred will be fertilized only from the other inbred (male), and the resulting seed is therefore hybrid and will form hybrid plants.

The laborious detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. The same hybrid seed, a portion produced from detasseled fertile maize and a portion produced using the CMS system can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. These and all patents referred to are incorporated by reference. In addition to these methods, Albertsen et al., of Pioneer Hi-Bred, U.S. Pat. No. 5,432,068, have developed a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329, 308 and PCT application PCT/CA90/00037 published as WO 90/08828).

Another system useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904). Application of the gametocide, timing of the application and genotype specificity often limit the usefulness of the approach and it is not appropriate in all situations.

The use of male sterile inbreds is but one factor in the production of maize hybrids. The development of maize hybrids in a maize plant breeding program requires, in general, the development of homozygous inbred lines, the crossing of these lines, and the evaluation of the crosses. Maize plant breeding programs combine the genetic backgrounds from two or more inbred lines or various other germplasm sources into breeding populations from which new inbred lines are developed by selfing and selection of desired phenotypes. Hybrids also can be used as a source of plant breeding material or as source populations from which to develop or derive new maize lines. Plant breeding techniques known in the art and used in a maize plant breeding program include, but are not limited to, recurrent selection, backcrossing, double haploids, pedigree breeding, restriction fragment length polymorphism enhanced selection, genetic marker enhanced selection, and transformation. Often a combination of these techniques are used. The inbred lines derived from hybrids can be developed using plant breeding techniques as described above. New inbreds are crossed with other inbred lines and the hybrids from these crosses are evaluated to determine which of those have commercial potential.

Backcrossing can be used to improve inbred lines and a hybrid which is made using those inbreds. Backcrossing can be used to transfer a specific desirable trait from one line, the donor parent, to an inbred called the recurrent parent which has overall good agronomic characteristics yet that lacks the desirable trait. This transfer of the desirable trait into an inbred with overall good agronomic characteristics can be accomplished by first crossing a recurrent parent to a donor parent (non-recurrent parent). The progeny of this cross is then mated back to the recurrent parent followed by selection in the resultant progeny for the desired trait to be transferred from the non-recurrent parent. Typically after four or more backcross generations with selection for the desired trait, the progeny will contain essentially all genes of the recurrent parent except for the genes controlling the desired trait. But the number of backcross generations can be less if molecular markers are used during the selection or elite germplasm is used as the donor parent. The last backcross generation is then selfed to give pure breeding progeny for the gene(s) being transferred.

Backcrossing can also be used in conjunction with pedigree breeding to develop new inbred lines. For example, an F1 can be created that is backcrossed to one of its parent lines to create a BC1. Progeny are selfed and selected so that the newly developed inbred has many of the attributes of the recurrent parent and some of the desired attributes of the non-recurrent parent.

Recurrent selection is a method used in a plant breeding program to improve a population of plants. The method entails individual plants cross pollinating with each other to form progeny which are then grown. The superior progeny are then selected by any number of methods, which include individual plant, half sib progeny, full sib progeny, selfed progeny and topcrossing. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds. Mass selection is a useful technique when used in conjunction with molecular marker enhanced selection.

Molecular markers including techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Single Nucleotide Polymorphisms (SNPs) and Simple Sequence Repeats (SSRs) may be used in plant breeding methods. One use of molecular markers is Quantitative Trait Loci (QTL) mapping. QTL mapping is the use of markers, which are closely linked to alleles that have measurable effects on a quantitative trait. Selection in the breeding process is based upon the accumulation of markers linked to the positive effecting alleles and/or the elimination of the markers linked to the negative effecting alleles from the plants genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection.

The production of double haploids can also be used for the development of inbreds in a breeding program. Double haploids are produced by the doubling of a set of chromosomes (1N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77: 889–892, 1989. This can be advantageous because the process can eliminate the generations of selfing needed to obtain a homozygous plant from a heterozygous source.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed. Also, because the male parent is grown next to the female parent in the field there is the very low probability that the male selfed seed could be unintentionally harvested and packaged with the hybrid seed. Once the seed from the hybrid bag is planted, it is possible to identify and select these self-pollinated plants. These self-pollinated plants will be genetically equivalent to one of the inbred lines used to produce the hybrid. Though the possibility of inbreds being included hybrid seed bags exists, the occurrence is very low because much care is taken to avoid such inclusions. It is worth noting that hybrid seed is sold to growers for the production of grain and forage and not for breeding or seed production.

By an individual skilled in plant breeding, these inbred plants unintentionally included in commercial hybrid seed can be identified and selected due to their decreased vigor when compared to the hybrid. Inbreds are identified by their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1–8 (1995), the disclosure of which is expressly incorporated herein by reference. Through these technologies, the homozygosity of the self pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritica si Aplicata Vol. 20 (1) p. 29–42.

Another form of commercial hybrid production involves the use of a mixture of male sterile hybrid seed and male pollinator seed. When planted, the resulting male sterile hybrid plants are pollinated by the pollinator plants. This method is primarily used to produce grain with enhanced quality grain traits, such as high oil, because desired quality grain traits expressed in the pollinator will also be expressed in the grain produced on the male sterile hybrid plant. In this method the desired quality grain trait does not have to be incorporated by lengthy procedures such as recurrent backcross selection into an inbred parent line. One use of this method is described U.S. Pat. Nos. 5,704,160 and 5,706,603.

There are many important factors to be considered in the art of plant breeding, such as the ability to recognize important morphological and physiological characteristics, the ability to design evaluation techniques for genotypic and phenotypic traits of interest, and the ability to search out and exploit the genes for the desired traits in new or improved combinations.

The objective of commercial maize hybrid line development resulting from a maize plant breeding program is to develop new inbred lines to produce hybrids that combine to produce high grain yields and superior agronomic performance. One of the primary traits breeders seek is yield. However, many other major agronomic traits are of importance in hybrid combination and have an impact on yield or otherwise provide superior performance in hybrid combinations. Such traits include percent grain moisture at harvest, relative maturity, resistance to stalk breakage, resistance to root lodging, grain quality, and disease and insect resistance. In addition, the lines per se must have acceptable performance for parental traits such as seed yields, kernel sizes, pollen production, all of which affect ability to provide parental lines in sufficient quantity and quality for hybridization. These traits have been shown to be under genetic control and many if not all of the traits are affected by multiple genes.

Pedigree Breeding

The pedigree method of breeding is the mostly widely used methodology for new hybrid line development.

In general terms this procedure consists of crossing two inbred lines to produce the non-segregating F1 generation, and self pollination of the F1 generation to produce the F2 generation that segregates for all factors for which the inbred parents differ. An example of this process is set forth below. Variations of this generalized pedigree method are used, but all these variations produce a segregating generation which contains a range of variation for the traits of interest.

EXAMPLE 1

Hypothetical Example of Pedigree Breeding Program

Consider a cross between two inbred lines that differ for alleles at six loci.

The parental genotypes are:

| Parent 1 | A b C d e F/A b C d e F |
| Parent 2 | a B c D E f/a B c D E f | the F1 from a cross between these two parents is:

| F1 | A b C d e F/a B c D E f |

Selfing F1 will produce an F2 generation including the following genotypes:

A B c D E f/a b C d e F
A B c D e f/a b C d E F
A B c D e f/ a b C d e F
.
.
.

The number of genotypes in the F2 is $3^6$ for six segregating loci (729) and will produce $(2^6)-2$ possible new inbreds, (62 for six segregating loci).

Each inbred parent which is used in breeding crosses represents a unique combination of genes, and the combined effects of the genes define the performance of the inbred and its performance in hybrid combination. There is published evidence (Smith, O. S., J. S. C. Smith, S. L. Bowen, R. A. Tenborg and S. J. Wall, *TAG* 80: 833–840 (1990)) that each of the lines are different and can be uniquely identified on the basis of genetically-controlled molecular markers.

It has been shown (Hallauer, Arnel R. and Miranda, J. B. Fo. Quantitative *Genetics in Maize Breeding*, Iowa State University Press, Ames Iowa, 1981) that most traits of economic value in maize are under the genetic control of multiple genetic loci, and that there are a large number of unique combinations of these genes present in elite maize germplasm. If not, genetic progress using elite inbred lines would no longer be possible. Studies by Duvick and Russell (Duvick, D. N., *Maydica* 37: 69–79, (1992); Russell, W. A., Maydica XXIX: 375–390 (1983)) have shown that over the last 50 years the rate of genetic progress in commercial hybrids has been between one and two percent per year.

The number of genes affecting the trait of primary economic importance in maize, grain yield, has been estimated to be in the range of 10–1000. Inbred lines which are used as parents for breeding crosses differ in the number and combination of these genes. These factors make the plant breeder's task more difficult. Compounding this is evidence that no one line contains the favorable allele at all loci, and that different alleles have different economic values depending on the genetic background and field environment in which the hybrid is grown. Fifty years of breeding experience suggests that there are many genes affecting grain yield and each of these has a relatively small effect on this trait. The effects are small compared to breeders' ability to measure grain yield differences in evaluation trials. Therefore, the parents of the breeding cross must differ at several of these loci so that the genetic differences in the progeny will be large enough that breeders can develop a line that increases the economic worth of its hybrids over that of hybrids made with either parent.

If the number of loci segregating in a cross between two inbred lines is n, the number of unique genotypes in the F2 generation is $3^n$ and the number of unique inbred lines from this cross is $\{(2^n)-2\}$. Only a very limited number of these combinations is commercially useful.

By way of example, if it is assumed that the number of segregating loci in F2 is somewhere between 20 and 50, and that each parent is fixed for half the favorable alleles, it is then possible to calculate the approximate probabilities of finding an inbred that has the favorable allele at $\{(n/2)+m\}$ loci, where n/2 is the number of favorable alleles in each of the parents and m is the number of additional favorable alleles in the new inbred. See Example 2 below. The number m is assumed to be greater than three because each allele has so small an effect that evaluation techniques are not sensitive enough to detect differences due to three or less favorable alleles. The probabilities in Example 2 are on the order of $10^{-5}$ or smaller and they are the probabilities that at least one genotype with (n/2)=m favorable alleles will exist.

To put this in perspective, the number of plants grown on 60 million acres (approximate United States corn acreage) at 25,000 plants/acre is $1.5 \times 10^{12}$.

Example 2

Probability of Finding an Inbred with m of n Favorable Alleles

Assume each parent has n/2 of the favorable alleles and only ½ of the combinations of loci are economically useful.

| No. of segregating loci (n) | No. of favorable alleles in Parents (n/2) | No. additional favorable alleles in new inbred | Probability that genotype occurs* |
|---|---|---|---|
| 20 | 10 | 14 | $3 \times 10^{-5}$ |
| 24 | 12 | 16 | $2 \times 10^{-5}$ |
| 28 | 14 | 18 | $1 \times 10^{-5}$ |
| 32 | 16 | 20 | $8 \times 10^{-6}$ |
| 36 | 18 | 22 | $5 \times 10^{-6}$ |
| 40 | 20 | 24 | $3 \times 10^{-6}$ |

-continued

| No. of segregating loci (n) | No. of favorable alleles in Parents (n/2) | No. additional favorable alleles in new inbred | Probability that genotype occurs* |
|---|---|---|---|
| 44 | 22 | 26 | $2 \times 10^{-6}$ |
| 48 | 24 | 28 | $1 \times 10^{-6}$ |

*Probability that a useful combination exists, does not include the probability of identifying this combination if it does exist.

The possibility of having a usably high probability of being able to identify this genotype based on replicated field testing would be most likely smaller than this, and is a function of how large a population of genotypes is tested and how testing resources are allocated in the testing program.

A breeder uses various methods to help determine which plants should be selected from the segregating populations and ultimately which inbred lines will be used to develop hybrids for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest. Experimental design methods are used to asses error so that differences between two inbred lines or two hybrid lines can be more accurately determined. Statistical analysis includes the calculation of mean values, determination of the statistical significance of the sources of variation, and the calculation of the appropriate variance components. Either a five or one percent significance level is customarily used to determine whether a difference that occurs for a given trait is real or due to the environment or experimental error. One of ordinary skill in the art of plant breeding would know how to evaluate the traits of two plant varieties to determine if there is no significant difference between the two traits expressed by those varieties. For example, see Fehr, Walt, Principles of Cultivar Development, p. 261–286 (1987) which is incorporated herein by reference. Mean trait values may be used to determine whether trait differences are significant, and preferably the traits are measured on plants grown under the same environmental conditions. Combining ability of a line, as well as the performance of the line per se, is a factor in the selection of improved maize inbreds. Combining ability refers to a line's contribution as a parent when crossed with other lines to form hybrids. The hybrids formed for the purpose of selecting superior lines are designated test crosses. One way of measuring combining ability is by using breeding values. Breeding values are based in part on the overall mean of a number of test crosses. This mean is then adjusted to remove environmental effects and it is adjusted for known genetic relationships among the lines.

Once such a line is developed its value to society is substantial since it is important to advance the germplasm base as a whole in order to maintain or improve traits such as yield, disease resistance, pest resistance and plant performance in extreme weather conditions.

SUMMARY OF THE INVENTION

According to the invention, there is provided a hybrid maize plant, designated as 32A85, produced by crossing two Pioneer Hi-Bred International, Inc. proprietary inbred maize lines GE515488 and GE687272. These lines, deposited with the American Type Culture Collection, (ATCC), Manassas, Va. 20110, have Accession Number PTA-1304 for GE515488 and Accession Number PTA-5532 for GE587272. This invention thus relates to the hybrid seed 32A85, the hybrid plant and its parts produced from the seed, and variants, mutants and trivial modifications of hybrid 32A85. This invention also relates to methods for producing a maize plant containing in its genetic material one or more transgenes and to the transgenic maize plants and their parts produced by that method. This invention further relates to methods for producing maize lines derived from hybrid maize line 32A85 and to the maize lines derived by the use of those methods. This hybrid maize plant is characterized by good white grain color, good quality grain characteristics, and excellent ability to stand throughout the season.

Definitions

Certain definitions used in the specification are provided below. In order to provide a clear and consistent understanding of the specification and claims, including the scope to be given such terms, the following definitions are provided. NOTE: ABS is in absolute terms and % MN is percent of the mean for the experiments in which the inbred or hybrid was grown. PCT designates that the trait is calculated as a percentage. % NOT designates the percentage of plants that did not exhibit trait. For example, STKLDG % NOT is the percentage of plants in a plot that were not stalk lodged. These designators will follow the descriptors to denote how the values are to be interpreted. Below are the descriptors used in the data tables included herein.

ABTSTK=ARTIFICIAL BRITTLE STALK. A count of the number of "snapped" plants per plot following machine snapping. A snapped plant has its stalk completely snapped at a node between the base of the plant and the node above the ear. Expressed as percent of plants that did not snap.

ADF=PERCENT ACID DETERGENT FIBER. The percent of dry matter that is acid detergent fiber in chopped whole plant forage.

ALLELE. Any of one or more alternative forms of a genetic sequence. In a diploid cell or organism, the two alleles of a given sequence occupy corresponding loci on a pair of homologous chromosomes.

ANT ROT=ANTHRACNOSE STALK ROT (*Colletotrichum graminicola*). A 1 to 9 visual rating indicating the resistance to Anthracnose Stalk Rot. A higher score indicates a higher resistance.

BACKCROSSING. Process in which a breeder crosses a progeny line back to one of the parental genotypes one or more times.

BARPLT=BARREN PLANTS. The percent of plants per plot that were not barren (lack ears).

BREEDING=The genetic manipulation of living organisms.

BRTSTK=BRITTLE STALKS. This is a measure of the stalk breakage near the time of pollination, and is an indication of whether a hybrid or inbred would snap or break near the time of flowering under severe winds. Data are presented as percentage of plants that did not snap.

CLDTST=COLD TEST. The percent of plants that germinate under cold test conditions CLN=CORN LETHAL NECROSIS (synergistic interaction of maize chlorotic mottle virus (MCMV) in combination with either maize dwarf mosaic virus (MDMV-A or MDMV-B) or wheat streak mosaic virus (WSMV)). A 1 to 9 visual rating indicating the resistance to Corn Lethal Necrosis. A higher score indicates a higher resistance.

COM RST=COMMON RUST (*Puccinia sorghi*). A 1 to 9 visual rating indicating the resistance to Common Rust. A higher score indicates a higher resistance.

CP=PERCENT OF CRUDE PROTEIN. The percent of dry matter that is crude protein in chopped whole plant forage.

D/D=DRYDOWN. This represents the relative rate at which a hybrid will reach acceptable harvest moisture compared to other hybrids on a 1–9 rating scale. A high score indicates a hybrid that dries relatively fast while a low score indicates a hybrid that dries slowly.

DIPERS=DIPLODIA EAR MOLD SCORES (*Diplodia maydis* and *Diplodia macrospora*). A 1 to 9 visual rating indicating the resistance to *Diplodia* Ear Mold. A higher score indicates a higher resistance.

DIPROT=DIPLODIA STALK ROT SCORE. Score of stalk rot severity due to *Diplodia* (*Diplodia maydis*). Expressed as a 1 to 9 score with 9 being highly resistant.

DM=PERCENT OF DRY MATTER. The percent of dry material in chopped whole plant silage.

DRPEAR=DROPPED EARS, A measure of the number of dropped ears per plot and represents the percentage of plants that did not drop ears prior to harvest.

D/T=DROUGHT TOLERANCE. This represents a 1–9 rating for drought tolerance, and is based on data obtained under stress conditions. A high score indicates good drought tolerance and a low score indicates poor drought tolerance.

EARHT=EAR HEIGHT. The ear height is a measure from the ground to the highest placed developed ear node attachment and is measured in centimeters.

EARMLD=General Ear Mold. Visual rating (1–9 score) where a "1" is very susceptible and a "9" is very resistant. This is based on overall rating for ear mold of mature ears without determining the specific mold organism, and may not be predictive for a specific ear mold.

EARSZ=EAR SIZE. A 1 to 9 visual rating of ear size. The higher the rating the larger the ear size.

EBTSTK=EARLY BRITTLE STALK. A count of the number of "snapped" plants per plot following severe winds when the corn plant is experiencing very rapid vegetative growth in the V5–V8 stage. Expressed as percent of plants that did not snap.

ECB1LF=EUROPEAN CORN BORER FIRST GENERATION LEAF FEEDING (*Ostrinia nubilalis*). A 1 to 9 visual rating indicating the resistance to preflowering leaf feeding by first generation European Corn Borer. A higher score indicates a higher resistance.

ECB2IT=EUROPEAN CORN BORER SECOND GENERATION INCHES OF TUNNELING (*Ostrinia nubilalis*). Average inches of tunneling per plant in the stalk.

ECB2SC=EUROPEAN CORN BORER SECOND GENERATION (*Ostrinia nubilalis*). A 1 to 9 visual rating indicating post flowering degree of stalk breakage and other evidence of feeding by European Corn Borer, Second Generation. A higher score indicates a higher resistance.

ECBDPE=EUROPEAN CORN BORER DROPPED EARS (*Ostrinia nubilalis*). Dropped ears due to European Corn Borer. Percentage of plants that did not drop ears under second generation corn borer infestation.

EGRWTH=EARLY GROWTH. The relative height and size of a corn seedling at the 2–4 leaf stage of growth. This is a visual rating (1 to 9), with 1 being weak or slow growth, 5 being average growth and 9 being strong growth. Taller plants, wider leaves, more green mass and darker color constitute higher scores.

ELITE INBRED=An inbred that contributed desirable qualities when used to produce commercial hybrids. An elite inbred may also be used in further breeding.

ERTLDG=EARLY ROOT LODGING. Early root lodging is the percentage of plants that do not root lodge prior to or around anthesis; plants that lean from the vertical axis at an approximately 30° angle or greater would be counted as root lodged.

ERTLPN=Early root lodging is an estimate of the percentage of plants that do not root lodge prior to or around anthesis; plants that lean from the vertical axis at an approximately 30° angle or greater would be considered as root lodged.

ERTLSC=EARLY ROOT LODGING SCORE. Score for severity of plants that lean from a vertical axis at an approximate 30 degree angle or greater which typically results from strong winds prior to or around flowering recorded within 2 weeks of a wind event. Expressed as a 1 to 9 score with 9 being no lodging.

ESTCNT=EARLY STAND COUNT. This is a measure of the stand establishment in the spring and represents the number of plants that emerge on per plot basis for the inbred or hybrid.

EYESPT=Eye Spot (*Kabatiella zeae* or *Aureobasidium zeae*). A 1 to 9 visual rating indicating the resistance to Eye Spot. A higher score indicates a higher resistance.

FUSERS=FUSARIUM EAR ROT SCORE (*Fusarium moniliforme* or *Fusarium subglutinans*). A 1 to 9 visual rating indicating the resistance to *Fusarium* ear rot. A higher score indicates a higher resistance.

GDU=Growing Degree Units. Using the Barger Heat Unit Theory, that assumes that maize growth occurs in the temperature range 50° F.–86° F. and that temperatures outside this range slow down growth; the maximum daily heat unit accumulation is 36 and the minimum daily heat unit accumulation is 0. The seasonal accumulation of GDU is a major factor in determining maturity zones.

GDUSHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp.})}{2} - 50$$

The highest maximum temperature used is 86° F. and the lowest minimum temperature used is 50° F. For each inbred or hybrid it takes a certain number of GDUs to reach various stages of plant development.

GDUSLK=GDU TO SILK. The number of growing degree units required for an inbred line or hybrid to have approximately 50 percent of the plants with silk emergence from time of planting. Growing degree units are calculated by the Barger Method as given in GDU SHD definition.

GENOTYPE. Refers to the genetic constitution of a cell or organism.

GIBERS=GIBBERELLA EAR ROT (PINK MOLD) (*Gibberella zeae*). A 1 to 9 visual rating indicating the resistance to *Gibberella* Ear Rot. A higher score indicates a higher resistance.

GIBROT=GIBBERELLA STALK ROT SCORE. Score of stalk rot severity due to *Gibberella* (*Gibberella zeae*). Expressed as a 1 to 9 score with 9 being highly resistant.

GLFSPT=Gray Leaf Spot (*Cercospora zeae-maydis*). A 1 to 9 visual rating indicating the resistance to Gray Leaf Spot. A higher score indicates a higher resistance.

GOSWLT=Goss' Wilt (*Corynebacterium nebraskense*). A 1 to 9 visual rating indicating the resistance to Goss' Wilt. A higher score indicates a higher resistance.

GRNAPP=GRAIN APPEARANCE. This is a 1 to 9 rating for the general appearance of the shelled grain as it is harvested based on such factors as the color of harvested grain, any mold on the grain, and any cracked grain. High scores indicate good grain quality.

H/POP=YIELD AT HIGH DENSITY. Yield ability at relatively high plant densities on 1–9 relative rating system with a higher number indicating the hybrid responds well to high plant densities for yield relative to other hybrids. A 1, 5, and 9 would represent very poor, average, and very good yield response, respectively, to increased plant density.

HCBLT=HELMINTHOSPORIUM CARBONUM LEAF BLIGHT (*Helminthosporium carbonum*). A 1 to 9 visual rating indicating the resistance to *Helminthosporium* infection. A higher score indicates a higher resistance.

HD SMT=Head Smut (*Sphacelotheca reiliana*). This score indicates the percentage of plants not infected.

HSKCVR=HUSK COVER. A 1 to 9 score based upon performance relative to key checks, with a score of 1 indicating very short husks, tip of ear and kernels showing; 5 is intermediate coverage of the ear under most conditions, sometimes with thin husk; and a 9 has husks extending and closed beyond the tip of the ear. Scoring can best be done near physiological maturity stage or any time during dry down until harvested.

KSZDCD=KERNEL SIZE DISCARD. The percent of discard seed; calculated as the sum of discarded tip kernels and extra large kernels.

LINKAGE. Refers to a phenomenon wherein alleles on the same chromosome tend to segregate together more often than expected by chance if their transmission was independent.

LINKAGE DISEQUILIBRIUM. Refers to a phenomenon wherein alleles tend to remain together in linkage groups when segregating from parents to offspring, with a greater frequency than expected from their individual frequencies.

L/POP=YIELD AT LOW DENSITY. Yield ability at relatively low plant densities on a 1–9 relative system with a higher number indicating the hybrid responds well to low plant densities for yield relative to other hybrids. A 1,5, and 9 would represent very poor, average, and very good yield response, respectively, to low plant density.

LRTLDG=LATE ROOT LODGING. Late root lodging is the percentage of plants that do not root lodge after anthesis through harvest; plants that lean from the vertical axis at an approximately 30° angle or greater would be counted as root lodged.

LRTLPN=LATE ROOT LODGING. Late root lodging is an estimate of the percentage of plants that do not root lodge after anthesis through harvest; plants that lean from the vertical axis at an approximately 30° angle or greater would be considered as root lodged.

LRTLSC=LATE ROOT LODGING SCORE. Score for severity of plants that lean from a vertical axis at an approximate 30 degree angle or greater which typically results from strong winds after flowering. Recorded prior to harvest when a root-lodging event has occurred. This lodging results in plants that are leaned or "lodged" over at the base of the plant and do not straighten or "goose-neck" back to a vertical position. Expressed as a 1 to 9 score with 9 being no lodging.

MDMCPX=Maize Dwarf Mosaic Complex (MDMV=Maize Dwarf Mosaic Virus and MCDV=Maize Chlorotic Dwarf Virus). A 1 to 9 visual rating indicating the resistance to Maize Dwarf Mosaic Complex. A higher score Indicates a higher resistance.

MST=HARVEST MOISTURE. The moisture is the actual percentage moisture of the grain at harvest.

MSTADV=MOISTURE ADVANTAGE. The moisture advantage of variety #1 over variety #2 as calculated by:

MOISTURE of variety #2—MOISTURE of variety #1=MOISTURE ADVANTAGE of variety #1.

NLFBLT=Northern Leaf Blight (*Helminthosporium turcicum* or *Exserohilum turcicum*). A 1 to 9 visual rating indicating the resistance to Northern Leaf Blight.

A higher score indicates a higher resistance.

OILT=GRAIN OIL. Absolute value of oil content of the kernel as predicted by Near-infrared Transmittance and expressed as a percent of dry matter.

PEDIGREE DISTANCE=Relationship among generations based on their ancestral links as evidenced in pedigrees. May be measured by the distance of the pedigree from a given starting point in the ancestry.

PLTHT=PLANT HEIGHT. This is a measure of the height of the plant from the ground to the tip of the tassel in centimeters.

POLSC=POLLEN SCORE. A 1 to 9 visual rating indicating the amount of pollen shed. The higher the score the more pollen shed.

POLWT=POLLEN WEIGHT. This is calculated by dry weight of tassels collected as shedding commences minus dry weight from similar tassels harvested after shedding is complete.

POP KIA=PLANT POPULATIONS. Measured as 1000s per acre.

POP ADV=PLANT POPULATION ADVANTAGE. The plant population advantage of variety #1 over variety #2 as calculated by PLANT POPULATION of variety #2—PLANT POPULATION of variety #1=PLANT POPULATION ADVANTAGE of variety #1.

PRM=PREDICTED RELATIVE MATURITY. This trait, predicted relative maturity, is based on the harvest moisture of the grain. The relative maturity rating is based on a known set of checks and utilizes standard linear regression analyses and also is referred to as the Comparative Relative Maturity Rating System that is similar to the Minnesota Relative Maturity Rating System.

PRMSHD=A relative measure of the growing degree units (GDU) required to reach 50% pollen shed. Relative values are predicted values from the linear regression of observed GDU's on relative maturity of commercial checks.

PROT=GRAIN PROTEIN. Absolute value of protein content of the kernel as predicted by Near-Infrared Transmittance and expressed as a percent of dry matter.

RTLDG=ROOT LODGING. Root lodging is the percentage of plants that do not root lodge; plants that lean from the vertical axis as an approximately 30° angle or greater would be counted as root lodged.

RTLADV=ROOT LODGING ADVANTAGE. The root lodging advantage of variety #1 over variety #2.

SCTGRN=SCATTER GRAIN. A 1 to 9 visual rating indicating the amount of scatter grain (lack of pollination or kernel abortion) on the ear. The higher the score the less scatter grain.

SDGVGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A maize breeder may utilize his or her own set of traits for the selection index. One of the traits that is almost always included is yield. The selection index data presented in the tables represent the mean value averaged across testing stations.

SIL DMP SILAGE DRY MATTER. The percent of dry material in chopped whole plant silage.

SLFBLT=SOUTHERN LEAF BLIGHT (*Helminthosporium maydis* or *Bipolaris maydis*). A 1 to 9 visual rating indicating the resistance to Southern Leaf Blight. A higher score indicates a higher resistance.

SOURST=SOUTHERN RUST (*Puccinia polysora*). A 1 to 9 visual rating indicating the resistance to Southern Rust. A higher score indicates a higher resistance.

STAGRN=STAY GREEN. Stay green is the measure of plant health near the time of black layer formation (physiological maturity). A high score indicates better late-season plant health.

STARCH=PERCENT OF STARCH. The percent of dry matter that is starch in chopped whole plant forage.

STDADV=STALK STANDING ADVANTAGE. The advantage of variety #1 over variety #2 for the trait STK CNT.

STKCNT=NUMBER OF PLANTS. This is the final stand or number of plants per plot.

STKLDG=STALK LODGING REGULAR. This is the percentage of plants that did not stalk lodge (stalk breakage at regular harvest (when grain moisture is between about 20 and 30%)) as measured by either natural lodging or pushing the stalks and determining the percentage of plants that break below the ear.

STKLDL=LATE STALK LODGING. This is the percentage of plants that did not stalk lodge (stalk breakage) at or around late season harvest (when grain moisture is between about 15 and 18%) as measured by either natural lodging or pushing the stalks and determining the percentage of plants that break below the ear.

STKLDS=STALK LODGING SCORE. A plant is considered as stalk lodged if the stalk is broken or crimped between the ear and the ground. This can be caused by any or a combination of the following: strong winds late in the season, disease pressure within the stalks, ECB damage or genetically weak stalks. This trait should be taken just prior to or at harvest. Expressed on a 1 to 9 scale with 9 being no lodging.

STLPCN=STALK LODGING REGULAR. This is an estimate of the percentage of plants that did not stalk lodge (stalk breakage at regular harvest (when grain moisture is between about 20 and 30%)) as measured by either natural lodging or pushing the stalks and determining the percentage of plants that break below the ear.

STRT=GRAIN STARCH. Absolute value of starch content of the kernel as predicted by Near-Infrared Transmittance and expressed as a percent of dry matter.

STWWLT=Stewart's Wilt (*Erwinia stewartii*). A 1 to 9 visual rating indicating the resistance to Stewart's Wilt. A higher score indicates a higher resistance.

TASBLS=TASSEL BLAST. A 1 to 9 visual rating was used to measure the degree of blasting (necrosis due to heat stress) of the tassel at the time of flowering. A 1 would indicate a very high level of blasting at time of flowering, while a 9 would have no tassel blasting.

TASSZ=TASSEL SIZE. A 1 to 9 visual rating was used to indicate the relative size of the tassel. The higher the rating the larger the tassel.

TASWT=TASSEL WEIGHT. This is the average weight of a tassel (grams) just prior to pollen shed.

TDM/HA=TOTAL DRY MATTER PER HECTARE. Yield of total dry plant material in metric tons per hectare.

TEXEAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data are given as a percentage of tillers: number of tillers per plot divided by number of plants per plot.

TST WT=TEST WEIGHT (UNADJUSTED). The measure of the weight of the grain in pounds for a given volume (bushel).

TSWADV=TEST WEIGHT ADVANTAGE. The test weight advantage of variety #1 over variety #2.

WIN M %=PERCENT MOISTURE WINS.

WIN Y %=PERCENT YIELD WINS.

YIELD=YIELD OF SILAGE. Yield in tons per acre at 30% dry matter.

YIELD BU/A=YIELD (BUSHELS/ACRE). Yield of the grain at harvest in bushels per acre adjusted to 15% moisture.

YLDADV=YIELD ADVANTAGE. The yield advantage of variety #1 over variety #2 as calculated by: YIELD of variety #1−YIELD variety #2=yield advantage of variety #1.

YLD SC=YIELD SCORE. A 1 to 9 visual rating was used to give a relative rating for yield based on plot ear piles. The higher the rating the greater visual yield appearance.

Definitions for Area of Adaptability

When referring to area of adaptability, such term is used to describe the location with the environmental conditions that would be well suited for this maize line. Area of adaptability is based on a number of factors, for example: days to maturity, insect resistance, disease resistance, and drought resistance. Area of adaptability does not indicate that the maize line will grow in every location within the area of adaptability or that it will not grow outside the area.

Central Corn Belt: Iowa, Illinois, Indiana

Drylands: non-irrigated areas of North Dakota, South Dakota, Nebraska, Kansas, Colorado and Oklahoma Eastern U.S.: Ohio, Pennsylvania, Delaware, Maryland, Virginia, and West Virginia North central U.S.: Minnesota and Wisconsin Northeast: Michigan, New York, Vermont, and Ontario and Quebec Canada Northwest U.S.: North Dakota, South Dakota, Wyoming, Washington, Oregon, Montana, Utah, and Idaho South central U.S.: Missouri, Tennessee, Kentucky, Arkansas Southeast U.S.: North Carolina, South Carolina, Georgia, Florida, Alabama, Mississippi, and Louisiana Southwest U.S.: Texas, Oklahoma, New Mexico, Arizona Western U.S.: Nebraska, Kansas, Colorado, and California Maritime Europe: France, Germany, Belgium, and Austria

DETAILED DESCRIPTION OF THE INVENTION

Inbred maize lines are typically developed for use in the production of hybrid maize lines. Maize hybrids need to be highly homogeneous, heterozygous and reproducible to be useful as commercial hybrids. There are many analytical methods available to determine the heterozygous nature and the identity of these lines.

The oldest and most traditional method of analysis is the observation of phenotypic traits. The data is usually collected in field experiments over the life of the maize plants to be examined. Phenotypic characteristics most often observed are for traits associated with plant morphology, ear and kernel morphology, insect and disease resistance, maturity, and yield.

In addition to phenotypic observations, the genotype of a plant can also be examined. A plants genotype can be used to identify plants of the same variety or a related variety. For example, the genotype can be used to determine the pedigree of a plant. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs).

Isozyme Electrophoresis and RFLPs as discussed in Lee, M., "Inbred Lines of Maize and Their Molecular Markers," *The Maize Handbook*, (Springer-Verlag, New York, Inc. 1994, at 423–432) incorporated herein by reference, have been widely used to determine genetic composition. Isozyme Electrophoresis has a relatively low number of available markers and a low number of allelic variants. RFLPs allow more discrimination because they have a higher degree of allelic variation in maize and a larger number of markers can be found. Both of these methods have been eclipsed by SSRs as discussed in Smith et al., "An evaluation of the utility of SSR loci as molecular markers in maize (*Zea mays* L.): comparisons with data from RFLPs and pedigree", *Theoretical and Applied Genetics* (1997) vol. 95 at 163–173 and by Pejic et al., "Comparative analysis of genetic similarity among maize inbreds detected by RFLPs, RAPDs, SSRs, and AFLPs," *Theoretical and Applied Genetics* (1998) at 1248–1255 incorporated herein by reference. SSR technology is more efficient and practical to use than RFLPs; more marker loci can be routinely used and more alleles per marker locus can be found using SSRs in comparison to RFLPs. Single Nucleotide Polymorphisms may also be used to identify the unique genetic composition of the invention and progeny lines retaining that unique genetic composition. Various molecular marker techniques may be used in combination to enhance overall resolution.

Maize DNA molecular marker linkage maps have been rapidly constructed and widely implemented in genetic studies. One such study is described in Boppenmaier, et al., "Comparisons among strains of inbreds for RFLPs", Maize Genetics Cooperative Newsletter, 65: 1991, pg. 90, is incorporated herein by reference.

Pioneer Brand Hybrid 32A85 is characterized by very good yield potential and excellent stalk lodging resistance. Hybrid 32A85 further demonstrates good plant health and stay green as well as good early growth. The hybrid also provides good grain quality and good food corn characteristics in addition to good resistance to head smut. The hybrid demonstrates very good drought tolerance and is particularly suited to the Central Corn Belt, Southcentral, Southwest, and Western regions of the United States.

Pioneer Brand Hybrid 32A85 is a single cross, white endosperm, dent maize hybrid. Hybrid 32A85 has a relative maturity of approximately 115 based on the Comparative Relative Maturity Rating System for harvest moisture of grain.

This hybrid has the following characteristics based on the data collected primarily at Johnston, Iowa.

TABLE 1

VARIETY DESCRIPTION INFORMATION
VARIETY = 32A85

1. TYPE: (describe intermediate types in Comments section):
   2  1 = Sweet 2 = Dent 3 = Flint 4 = Flour 5 = Pop 6 = Ornamental
2. MATURITY:

| DAYS | HEAT UNITS | |
|---|---|---|
| 069 | 1,369.7 | From emergence to 50% of plants in silk |
| 068 | 1,345.3 | From emergence to 50% of plants in pollen |
| 002 | 0,042.7 | From 10% to 90% pollen shed |
|   |   | From 50% silk to harvest at 25% moisture |

3. PLANT:

| | | Standard Deviation | Sample Size |
|---|---|---|---|
| 0,295.7 cm | Plant Height (to tassel tip) | 14.29 | 15 |
| 0,108.0 cm | Ear Height (to base of top ear node) | 11.53 | 15 |
| 0,019.4 cm | Length of Top Ear Internode | 1.22 | 15 |
| 0.1 | Average Number of Tillers per plant | 0.02 | 3 |
| 1.0 | Average Number of Ears per Stalk | 0.14 | 3 |
| 2.0 | Anthocyanin of Brace Roots: 1 = Absent 2 = Faint 3 = Moderate 4 = Dark 5 = Very Dark | | |

4. LEAF:

| | | Standard Deviation | Sample Size |
|---|---|---|---|
| 010.8 cm | Width of Ear Node Leaf | 0.72 | 15 |
| 091.4 cm | Length of Ear Node Leaf | 5.92 | 15 |
| 07.8 | Number of leaves above top ear | 0.87 | 15 |
| 018.9 | Degrees Leaf Angle (measure from 2nd leaf above ear at anthesis to stalk above leaf) | 2.00 | 15 |
| 03 | Leaf Color  Dark Green  (Munsell code)  5GY36 | | |
| 1.7 | Leaf Sheath Pubescence (Rate on scale from 1 = none to 9 = like peach fuzz) Marginal Waves (Rate on scale from 1 = none to 9 = many) Longitudinal Creases (Rate on scale from 1 = none to 9 = many) | | |

5. TASSEL:

| | | Standard Deviation | Sample Size |
|---|---|---|---|
| 05.2 | Number of Primary Lateral Branches | 1.59 | 15 |
| 028.3 | Branch Angle from Central Spike | 7.32 | 15 |
| 68.7 cm | Tassel Length (from top leaf collar to tassel tip) | 3.23 | 15 |
| 5.0 | Pollen Shed (rate on scale from 0 = male sterile to 9 = heavy shed) | | |
| 01 | Anther Color  Light Green  (Munsell code)  2.5GY78 | | |
| 17 | Glume Color  Purple  (Munsell code)  10RP26 | | |
| 1.0 | Bar Glumes (Glume Bands): 1 = Absent 2 = Present | | |
| 30 cm | Peduncle Length (cm. from top leaf to basal branches) | | |

6a. EAR (Unhusked Data):
| | | | | |
|---|---|---|---|---|
| 1 | Silk Color (3 days after emergence) | Light Green | (Munsell code) | 2.5GY88 |
| 1 | Fresh Husk Color (25 days after 50% silking) | Light Green | (Munsell code) | 5GY68 |
| 21 | Dry Husk Color (65 days after 50% silking) | Buff | (Munsell code) | 5Y8.52 |
| 2 | Position of Ear at Dry Husk Stage: 1 = Upright 2 = Horizontal 3 = Pendant | | | Horizontal |
| 6 | Husk Tightness (Rate of Scale from 1 = very loose to 9 = very tight) | | | |
| 2 | Husk Extension (at harvest): 1 = Short (ears exposed) 2 = Medium (<8 cm) 3 = Long (8–10 cm beyond ear tip) 4 = Very Long (>10 cm) | | | Medium |

6b. EAR (Husked Ear Data):

| | | Standard Deviation | Sample Size | |
|---|---|---|---|---|
| 16 cm | Ear Length | 2.65 | 15 | |
| 47 mm | Ear Diameter at mid-point | 2.52 | 15 | |
| 170 gm | Ear Weight | 64.7 | 15 | |
| 18 | Number of Kernel Rows | 1.53 | 15 | |
| 2 | Kernel Rows: 1 = Indistinct 2 = Distinct | | | Distinct |
| 2 | Row Alignment: 1 = Straight 2 = Slightly Curved 3 = Spiral | | | Slightly Curved |
| 12 cm | Shank Length | 3.61 | 15 | |
| 1 | Ear Taper: 1 = Slight 2 = Average 3 = Extreme | | | Slight |

7. KERNEL (Dried):

| | | Standard Deviation | Sample Size |
|---|---|---|---|
| 13 mm | Kernel Length | 1.53 | 15 |
| 7 mm | Kernel Width | 0.58 | 15 |
| 5 mm | Kernel Thickness | 0.58 | 15 |
| 34 | % Round Kernels (Shape Grade) | 16.1 | 3 |
| 1 | Aleurone Color Pattern: 1 = Homozygous 2 = Segregating | | Homozygous |
| 19 | Aluerone Color  White  (Munsell code)  2.5Y8.52 | | |
| 19 | Hard Endosperm Color  White  (Munsell code)  5Y8.52 | | |
| 3 | Endosperm Type: Normal Starch 1 = Sweet (Su1) 2 = Extra Sweet (sh2) 3 = Normal Starch 4 = High Amylose Starch 5 = Waxy Starch 6 = High Protein 7 = High Lysine 8 = Super Sweet (se) 9 = High Oil 10 = Other _____ | | |

TABLE 1-continued

VARIETY DESCRIPTION INFORMATION
VARIETY = 32A85

| | | | | | |
|---|---|---|---|---|---|
| 31 gm | Weight per 100 Kernels (unsized sample) | | 2.52 | 3 | |
| | | | Standard | Sample | |
| 8. COB: | | | Deviation | Size | |
| 27 mm | Cob Diameter at mid-point | | 0.00 | 15 | |
| 19 | Cob Color | White | (Munsell code) | | 5Y91 |

9. DISEASE RESISTANCE (Rate from 1 (most susceptible) to 9 (most resistant); leave blank if not tested; leave Race or Strain Options blank if polygenic):
    A. Leaf Blights, Wilts, and Local Infection Diseases
            Anthracnose Leaf Blight (*Colletotrichum graminicola*)
        5 Common Rust (*Puccinia sorghi*)
            Common Smut (*Ustilago maydis*)
            Eyespot (*Kabatiella zeae*)
            Goss's Wilt (*Clavibacter michiganense* spp. *nebraskense*)
        5 Gray Leaf Spot (*Cercospora zeae-maydis*)
            Helminthosporium Leaf Spot (*Bipolaris zeicola*) Race _____
        3 Northern Leaf Blight (*Exserohilum turcicum*) Race _____
        5 Southern Leaf Blight (*Bipolaris maydis*) Race _____
            Southern Rust (*Puccinia polysora*)
            Stewart's Wilt (*Erwinia stewartii*)
            Other (Specify) _____
    B. Systemic Diseases
        3 Corn Lethal Necrosis (MCMV and MDMV)
            Head Smut (*Sphacelotheca reiliana*)
            Maize Chlorotic Dwarf Virus (MDV)
            Maize Chlorotic Mottle Virus (MCMV)
        2 Maize Dwarf Mosaic Virus (MDMV)
            Sorghum Downy Mildew of Corn
            (*Peronosclerospora sorghi*)
            Other (Specify) _____
    C. Stalk Rots
        5 Anthracnose Stalk Rot (*Colletotrichum graminicola*)
            Diplodia Stalk Rot (*Stenocarpella maydis*)
            *Fusarium* Stalk Rot (*Fusarium moniliforme*)
            *Gibberella* Stalk Rot (*Gibberella zeae*)
            Other (Specify) _____
    D. Ear and Kernel Rots
            *Aspergillus* Ear and Kernel Rot (*Aspergillus flavus*)
        3 Diplodia Ear Rot (*Stenocarpella maydis*)
        4 *Fusarium* Ear and Kernel Rot (*Fusarium moniliforme*)
            *Gibberella* Ear Rot (*Gibberella zeae*)
            Other (Specify) _____
Application Variety Data
10. INSECT RESISTANCE (Rate from 1 (most susceptible) to 9 (most resistant); (leave blank if not tested):
            Banks grass Mite (*Oligonychus pratensis*)
            Corn Worm (*Helicoverpa zea*)
            Leaf Feeding
            Silk Feeding
            mg larval wt.
            Ear Damage
            Corn Leaf Aphid (*Rhopalosiphum maidis*)
            Corn Sap Beetle (*Carpophilus dimidiatus*)
            European Corn Borer (*Ostrinia nubilalis*)
        5 1st Generation (Typically Whorl Leaf Feeding)
        7 2nd Generation (Typically Leaf Sheath-Collar Feeding)
            Stalk Tunneling
            cm tunneled/plant
            Fall Armyworm (*Spodoptera fruqiperda*)
            Leaf Feeding
            Silk Feeding
            mg larval wt.
            Maize Weevil (*Sitophilus zeamaize*)
            Northern Rootworm (*Diabrotica barberi*)
            Southern Rootworm (*Diabrotica undecimpunctata*)
            Southwestern Corn Borer (*Diatreaea grandiosella*)
            Leaf Feeding
            Stalk Tunneling
            cm tunneled/plant
            Two-spotted Spider Mite (*Tetranychus urticae*)
            Western Rootworm (*Diabrotica virgifrea virgifera*)
            Other (Specify) _____
11. AGRONOMIC TRAITS:
        6 Staygreen (65 days after anthesis. Rate on a scale from
            1 = worst to 9 = excellent)
        0.0 % Dropped Ears (at 65 days after anthesis)

TABLE 1-continued

VARIETY DESCRIPTION INFORMATION
VARIETY = 32A85

% Pre-anthesis Brittle Snapping
% Pre-anthesis Root Lodging
3.5 Post-anthesis Root Lodging (at 65 days after anthesis)
11,375 Kg/ha Yield (at 12–13% grain moisture)
Application Variety Data Research Comparisons for Pioneer Hybrid 32A85

Comparisons of characteristics for Pioneer Brand Hybrid 32A85 were made against Pioneer Brand Hybrids 32H39, 33T17, 32Y52, and 32K72.

Table 2A compares hybrid 32A85 with 32H39 a closely related hybrid with solid agronomic traits. The table indicates that hybrid 32A85 is significantly higher yielding (BU/A ABS and BU/A % MN) than hybrid 32H39. Hybrid 32A85 also exhibits a significantly higher number of growing degree units to pollen shed and a significantly taller plant stature than hybrid 32H39. Hybrid 32A85 further demonstrates significantly better stay green and a significantly higher stalk count than hybrid 32H39. Hybrid 32A85 also provides significantly superior stalk lodging resistance (STKLDS and STLPCN) as well as significantly better tolerance to late season root lodging than hybrid 32H39. 32A85 provides significantly better resistance to Gray Leaf Spot than 32H39.

Table 2B compares hybrid 32A85 with 33T17 a closely related hybrid with solid agronomic traits. The table indicates that hybrid 32A85 exhibits significantly superior stay green and a significantly higher number of growing degree units to pollen shed than hybrid 33T17. Hybrid 32A85 provides significantly lower ear placement and significantly superior stalk lodging resistance (STKLDS, and STLPCN) as well as significantly better late season stalk lodging resistance (STKLDL % NOT % MN) than hybrid 33T17. Hybrid 32A85 exhibits significantly better tolerance to Gray Leaf Spot, and to Anthracnose Stalk Rot than 33T17.

Table 2C compares hybrid 32A85 with 32Y52 a closely related hybrid with solid agronomic traits. The table indicates that hybrid 32A85 is significantly higher yielding BU/A ABS and BU/A % MN) than hybrid 32Y52. Hybrid 32A85 also exhibits significantly lower number of growing degree units to pollen shed than hybrid 32Y52. Hybrid 32A85 further demonstrates significantly better stay green and a significantly higher stalk count than hybrid 32Y52. Hybrid 32A85 also provides significantly lower ear placement and significantly superior stalk lodging resistance (STKLDS and STKLDG) as well as significantly better late season stalk lodging resistance (STKLDL % NOT % MN) than hybrid 32Y52. Hybrid 32A85 further exhibits significantly better tolerance to artificial brittle snap and significantly better tolerance to Anthracnose Stalk Rot and to European corn Borer second generation than hybrid 32Y52.

Table 2D compares hybrid 32A85 with 32K72 a closely related hybrid with solid agronomic traits. The table indicates that hybrid 32A85 is significantly higher yielding than hybrid 32K72. Hybrid 32A85 further demonstrates significantly better stay green and significantly higher stalk count than hybrid 32K72. Hybrid 32A85 also provides significantly superior stalk lodging resistance (STKLDS, and STLPCN) as well as significantly better late season stalk lodging resistance (STKLDL % NOT % MN) than hybrid 32K72. Hybrid 32A85 exhibits significantly better tolerance to Gray Leaf Spot and a significantly taller plant stature than hybrid 32K72.

TABLE 2A

HYBRID COMPARISON
Variety #1: 32A85
Variety #2: 32H39

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN | STKCNT COUNT % MN | PLTHT IN % MN | EARHT IN % MN |
|---|---|---|---|---|---|---|---|---|---|---|
| Mean1 | 181.0 | 99.6 | 103.7 | 107.3 | 99.1 | 101.2 | 100.0 | 101.0 | 101.1 | 96.0 |
| Mean2 | 163.8 | 89.8 | 101.2 | 101.4 | 100.0 | 97.3 | 98.6 | 99.0 | 93.5 | 95.9 |
| Locs | 218 | 218 | 221 | 25 | 7 | 51 | 31 | 316 | 61 | 61 |
| Reps | 218 | 218 | 221 | 25 | 7 | 51 | 31 | 316 | 61 | 61 |
| Diff | 17.2 | 9.8 | -2.5 | 5.9 | -0.9 | 3.9 | 1.5 | 1.9 | 7.6 | 0.2 |
| Prob | 0.000 | 0.000 | 0.000 | 0.127 | 0.834 | 0.000 | 0.075 | 0.000 | 0.000 | 0.880 |

| Stat | STAGRN SCORE % MN | ERTLSC SCORE ABS | LRTLSC SCORE ABS | STKLDS SCORE ABS | STKLDG % NOT % MN | STKLDL % NOT % MN | EBTSTK % NOT % MN | ABTSTK % NOT % MN | DRPEAR % NOT % MN | TSTWT LB/BU ABS |
|---|---|---|---|---|---|---|---|---|---|---|
| Mean1 | 119.6 | 4.0 | 7.0 | 7.8 | 103.7 | 120.0 | 98.1 | 138.8 | 100.1 | 56.9 |
| Mean2 | 101.5 | 5.0 | 4.0 | 6.5 | 105.7 | 117.3 | 103.0 | 84.1 | 99.1 | 57.6 |
| Locs | 60 | 1 | 3 | 33 | 19 | 47 | 1 | 8 | 3 | 165 |
| Reps | 60 | 1 | 3 | 33 | 19 | 47 | 1 | 8 | 3 | 165 |
| Diff | 18.1 | -1.0 | 3.0 | 1.4 | -2.1 | 2.8 | -4.9 | 54.8 | 1.1 | -0.7 |
| Prob | 0.000 | | 0.095 | 0.001 | 0.431 | 0.634 | | 0.007 | 0.184 | 0.000 |

| | GLFSPT | NLFBLT | SLFBLT | ANTROT | CLN | MDMCPX | FUSERS | DIPERS | COMRST | ECB1LF |

TABLE 2A-continued

HYBRID COMPARISON
Variety #1: 32A85  
Variety #2: 32H39

| Stat | SCORE ABS | SCORE ABS | SCORE ABS | SCORE ABS | SCORE ABS | SCORE ABS | SCORE ABS | SCORE ABS | SCORE ABS | SCORE ABS |
|---|---|---|---|---|---|---|---|---|---|---|
| Mean1 | 5.4 | 3.3 | 4.8 | 5.3 | 3.1 | 1.8 | 4.5 | 2.5 | 5.0 | 5.3 |
| Mean2 | 4.6 | 4.6 | 4.9 | 5.0 | 4.3 | 2.5 | 5.0 | 4.8 | 3.5 | 5.1 |
| Locs | 20 | 8 | 4 | 12 | 2 | 3 | 16 | 2 | 2 | 3 |
| Reps | 20 | 8 | 4 | 12 | 2 | 3 | 16 | 2 | 2 | 3 |
| Diff | 0.8 | −1.3 | −0.1 | 0.3 | −1.1 | −0.7 | −0.5 | −2.3 | 1.5 | 0.3 |
| Prob | 0.003 | 0.029 | 0.789 | 0.482 | 0.500 | 0.057 | 0.277 | 0.421 | 0.205 | 0.199 |

| Stat | ECB2SC SCORE ABS | HSKCVR SCORE ABS | BRTSTK % NOT ABS | HD SMT % NOT ABS | ERTLPN % NOT ABS | LRTLPN % NOT ABS | STLPCN % NOT ABS |
|---|---|---|---|---|---|---|---|
| Mean1 | 6.5 | 5.3 | 93.0 | 95.5 | 94.0 | 96.5 | 90.0 |
| Mean2 | 5.8 | 5.3 | 93.7 | 94.4 | 85.0 | 82.6 | 81.8 |
| Locs | 13 | 25 | 2 | 6 | 5 | 17 | 49 |
| Reps | 13 | 25 | 2 | 6 | 5 | 17 | 49 |
| Diff | 0.7 | 0.0 | −0.6 | 1.1 | 9.0 | 13.8 | 8.2 |
| Prob | 0.141 | 1.000 | 0.505 | 0.771 | 0.181 | 0.003 | 0.010 |

TABLE 2B

HYBRID COMPARISON
Variety #1: 32A85  
Variety #2: 33T17

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN | STKCNT COUNT % MN | PLTHT IN % MN | EARHT IN % MN |
|---|---|---|---|---|---|---|---|---|---|---|
| Mean1 | 180.8 | 99.4 | 103.7 | 107.3 | 99.1 | 101.2 | 100.0 | 101.0 | 101.1 | 96.0 |
| Mean2 | 180.8 | 99.1 | 97.0 | 107.3 | 98.1 | 99.5 | 99.5 | 100.6 | 100.0 | 101.8 |
| Locs | 219 | 219 | 224 | 25 | 7 | 51 | 31 | 319 | 61 | 61 |
| Reps | 219 | 219 | 224 | 25 | 7 | 51 | 31 | 319 | 61 | 61 |
| Diff | −0.0 | 0.4 | −6.6 | 0.0 | 0.9 | 1.7 | 0.5 | 0.4 | 1.1 | −5.8 |
| Prob | 0.981 | 0.661 | 0.000 | 0.994 | 0.665 | 0.000 | 0.402 | 0.226 | 0.078 | 0.000 |

| Stat | STAGRN SCORE % MN | ERTLSC SCORE ABS | LRTLSC SCORE ABS | STKLDS SCORE ABS | STKLDG % NOT % MN | STKLDL % NOT % MN | EBTSTK % NOT % MN | ABTSTK % NOT % MN | DRPEAR % NOT % MN | TSTWT LB/BU ABS |
|---|---|---|---|---|---|---|---|---|---|---|
| Mean1 | 119.6 | 4.0 | 7.0 | 7.8 | 103.6 | 118.0 | 98.1 | 138.8 | 100.1 | 56.9 |
| Mean2 | 82.5 | 8.0 | 4.7 | 5.7 | 98.2 | 98.4 | 103.1 | 126.8 | 100.1 | 57.6 |
| Locs | 60 | 1 | 3 | 33 | 20 | 50 | 1 | 8 | 3 | 165 |
| Reps | 60 | 1 | 3 | 33 | 20 | 50 | 1 | 8 | 3 | 165 |
| Diff | 37.1 | −4.0 | 2.3 | 2.2 | 5.4 | 19.7 | −5.0 | 12.0 | 0.0 | −0.6 |
| Prob | 0.000 |  | 0.250 | 0.000 | 0.062 | 0.000 |  | 0.059 | 1.000 | 0.000 |

| Stat | GLFSPT SCORE ABS | NLFBLT SCORE ABS | SLFBLT SCORE ABS | ANTROT SCORE ABS | CLN SCORE ABS | MDMCPX SCORE ABS | FUSERS SCORE ABS | DIPERS SCORE ABS | COMRST SCORE ABS | ECB1LF SCORE ABS |
|---|---|---|---|---|---|---|---|---|---|---|
| Mean1 | 5.4 | 3.3 | 4.8 | 5.2 | 3.1 | 1.8 | 4.5 | 2.5 | 5.0 | 5.3 |
| Mean2 | 4.7 | 3.3 | 4.4 | 4.1 | 3.4 | 2.7 | 5.3 | 3.3 | 4.0 | 5.3 |
| Locs | 21 | 8 | 4 | 13 | 2 | 3 | 16 | 2 | 2 | 3 |
| Reps | 21 | 8 | 4 | 13 | 2 | 3 | 16 | 2 | 2 | 3 |
| Diff | 0.6 | −0.1 | 0.4 | 1.1 | −0.3 | −0.8 | −0.9 | −0.8 | 1.0 | 0.0 |
| Prob | 0.018 | 0.890 | 0.547 | 0.029 | 0.795 | 0.038 | 0.088 | 0.205 | 1.000 | 1.000 |

| Stat | ECB2SC SCORE ABS | HSKCVR SCORE ABS | BRTSTK % NOT ABS | HD SMT % NOT ABS | ERTLPN % NOT ABS | LRTLPN % NOT ABS | STLPCN % NOT ABS |
|---|---|---|---|---|---|---|---|
| Mean1 | 6.5 | 5.3 | 93.0 | 95.5 | 94.0 | 96.5 | 89.8 |
| Mean2 | 5.5 | 5.4 | 84.0 | 97.0 | 80.0 | 85.6 | 74.6 |
| Locs | 13 | 25 | 2 | 6 | 5 | 17 | 48 |
| Reps | 13 | 25 | 2 | 6 | 5 | 17 | 48 |

TABLE 2B-continued

HYBRID COMPARISON
Variety #1: 32A85
Variety #2: 33T17

|      |       |       |       |       |       |       |       |
|------|-------|-------|-------|-------|-------|-------|-------|
| Diff | 1.0   | −0.1  | 9.0   | −1.5  | 14.0  | 10.9  | 15.2  |
| Prob | 0.012 | 0.621 | 0.448 | 0.558 | 0.206 | 0.107 | 0.000 |

TABLE 2C

HYBRID COMPARISON
Variety #1: 32A85
Variety #2: 32Y52

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN | STKCNT COUNT % MN | PLTHT IN % MN | EARHT IN % MN | STAGRN SCORE % MN | ERTLSC SCORE ABS |
|---|---|---|---|---|---|---|---|---|---|---|---|---|
| Mean1 | 180.7 | 103.2 | 104.6 | 108.6 | 99.1 | 100.5 | 99.3 | 101.4 | 102.4 | 98.8 | 123.8 | 4.0 |
| Mean2 | 172.8 | 97.8 | 103.5 | 110.9 | 100.9 | 102.2 | 100.1 | 99.4 | 100.0 | 107.0 | 94.2 | 7.0 |
| Locs | 91 | 91 | 94 | 12 | 7 | 17 | 12 | 134 | 23 | 23 | 27 | 1 |
| Reps | 91 | 91 | 94 | 12 | 7 | 17 | 12 | 134 | 23 | 23 | 27 | 1 |
| Diff | 7.9 | 5.4 | −1.1 | −2.3 | −1.8 | −1.7 | −0.9 | 2.0 | 2.4 | −8.2 | 29.6 | −3.0 |
| Prob | 0.001 | 0.000 | 0.231 | 0.787 | 0.706 | 0.007 | 0.251 | 0.008 | 0.017 | 0.000 | 0.001 |  |

| Stat | LRTLSC SCORE ABS | STKLDS SCORE ABS | STKLDG % NOT % MN | STKLDL % NOT % MN | EBTSTK % NOT % MN | ABTSTK % NOT % MN | DRPEAR % NOT % MN | TSTWT LB/BU ABS | GLFSPT SCORE ABS | NLFBLT SCORE ABS | SLFBLT SCORE ABS | ANTROT SCORE ABS |
|---|---|---|---|---|---|---|---|---|---|---|---|---|
| Mean1 | 7.0 | 8.1 | 104.9 | 116.7 | 98.1 | 135.6 | 100.1 | 56.7 | 4.6 | 4.2 | 4.5 | 5.0 |
| Mean2 | 5.0 | 6.6 | 100.0 | 96.6 | 96.5 | 96.4 | 99.2 | 57.0 | 4.0 | 4.3 | 3.0 | 3.3 |
| Locs | 3 | 30 | 14 | 20 | 1 | 5 | 2 | 62 | 6 | 3 | 1 | 8 |
| Reps | 3 | 30 | 14 | 20 | 1 | 5 | 2 | 62 | 6 | 3 | 1 | 8 |
| Diff | 2.0 | 1.5 | 5.0 | 20.1 | 1.6 | 39.2 | 0.8 | −0.3 | 0.6 | −0.2 | 1.5 | 1.8 |
| Prob | 0.074 | 0.000 | 0.050 | 0.020 |  | 0.003 | 0.500 | 0.137 | 0.341 | 0.840 |  | 0.032 |

| Stat | CLN SCORE ABS | MDMCPX SCORE ABS | FUSERS SCORE ABS | DIPERS SCORE ABS | COMRST SCORE ABS | ECB1LF SCORE ABS | ECB2SC SCORE ABS | HSKCVR SCORE ABS | BRTSTK % NOT ABS | HD SMT % NOT ABS |
|---|---|---|---|---|---|---|---|---|---|---|
| Mean1 | 2.8 | 2.0 | 4.5 | 2.5 | 4.0 | 6.0 | 5.0 | 5.0 | 88.7 | 95.3 |
| Mean2 | 4.5 | 2.5 | 4.7 | 3.5 | 3.0 | 6.3 | 4.8 | 5.5 | 100.0 | 78.9 |
| Locs | 1 | 1 | 3 | 1 | 1 | 2 | 2 | 10 | 1 | 2 |
| Reps | 1 | 1 | 3 | 1 | 1 | 2 | 2 | 10 | 1 | 2 |
| Diff | −1.8 | −0.5 | −0.2 | −1.0 | 1.0 | −0.3 | 0.3 | −0.5 | −11.3 | 16.4 |
| Prob |  |  | 0.808 |  |  | 0.500 | 0.500 | 0.052 |  | 0.444 |

TABLE 2D

HYBRID COMPARISON
Variety #1: 32A85
Variety #2: 32K72

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN | STKCNT COUNT % MN | PLTHT IN % MN | EARHT IN % MN |
|---|---|---|---|---|---|---|---|---|---|---|
| Mean1 | 181.2 | 99.6 | 103.8 | 107.9 | 99.1 | 101.1 | 99.9 | 101.0 | 101.1 | 96.1 |
| Mean2 | 177.0 | 96.6 | 101.0 | 112.5 | 103.2 | 101.0 | 99.7 | 99.3 | 99.0 | 98.4 |
| Locs | 215 | 215 | 218 | 23 | 7 | 49 | 29 | 315 | 59 | 59 |
| Reps | 215 | 215 | 218 | 23 | 7 | 49 | 29 | 315 | 59 | 59 |
| Diff | 4.1 | 2.9 | −2.9 | −4.6 | −4.2 | 0.2 | 0.2 | 1.7 | 2.1 | −2.3 |
| Prob | 0.004 | 0.001 | 0.000 | 0.296 | 0.580 | 0.622 | 0.804 | 0.000 | 0.003 | 0.037 |

| Stat | STAGRN SCORE % MN | ERTLSC SCORE ABS | LRTLSC SCORE ABS | STKLDS SCORE ABS | STKLDG % NOT % MN | STKLDL % NOT % MN | EBTSTK % NOT % MN | ABTSTK % NOT % MN | DRPEAR % NOT % MN | TSTWT LB/BU ABS |
|---|---|---|---|---|---|---|---|---|---|---|
| Mean1 | 120.8 | 4.0 | 7.0 | 8.1 | 102.8 | 118.5 | 98.1 | 138.8 | 100.1 | 56.9 |
| Mean2 | 81.6 | 9.0 | 5.7 | 6.9 | 96.9 | 105.6 | 96.9 | 136.5 | 100.1 | 57.2 |
| Locs | 57 | 1 | 3 | 31 | 18 | 49 | 1 | 8 | 3 | 168 |
| Reps | 57 | 1 | 3 | 31 | 18 | 49 | 1 | 8 | 3 | 168 |

TABLE 2D-continued

HYBRID COMPARISON
Variety #1: 32A85
Variety #2: 32K72

| Stat | | | | | | | | | | |
|---|---|---|---|---|---|---|---|---|---|---|
| Diff | 39.2 | −5.0 | 1.3 | 1.1 | 5.9 | 12.9 | 1.2 | 2.4 | 0.0 | −0.3 |
| Prob | 0.000 | | 0.456 | 0.012 | 0.081 | 0.019 | | 0.316 | 1.000 | 0.024 |

| Stat | GLFSPT SCORE ABS | NLFBLT SCORE ABS | SLFBLT SCORE ABS | ANTROT SCORE ABS | CLN SCORE ABS | MDMCPX SCORE ABS | FUSERS SCORE ABS | DIPERS SCORE ABS | COMRST SCORE ABS | ECB1LF SCORE ABS |
|---|---|---|---|---|---|---|---|---|---|---|
| Mean1 | 5.4 | 3.3 | 4.8 | 5.2 | 3.1 | 1.8 | 4.3 | 2.5 | 5.0 | 5.3 |
| Mean2 | 3.6 | 3.1 | 3.4 | 4.5 | 4.0 | 1.8 | 4.2 | 3.8 | 4.5 | 5.4 |
| Locs | 21 | 8 | 4 | 13 | 2 | 3 | 14 | 2 | 2 | 3 |
| Reps | 21 | 8 | 4 | 13 | 2 | 3 | 14 | 2 | 2 | 3 |
| Diff | 1.8 | 0.1 | 1.4 | 0.7 | −0.9 | 0.0 | 0.1 | −1.3 | 0.5 | −0.1 |
| Prob | 0.000 | 0.626 | 0.115 | 0.191 | 0.500 | 1.000 | 0.810 | 0.126 | 0.500 | 0.423 |

| Stat | ECB2SC SCORE ABS | HSKCVR SCORE ABS | BRTSTK % NOT ABS | HD SMT % NOT ABS | ERTLPN % NOT ABS | LRTLPN % NOT ABS | STLPCN % NOT ABS |
|---|---|---|---|---|---|---|---|
| Mean1 | 6.5 | 5.3 | 93.0 | 95.5 | 94.0 | 96.5 | 90.0 |
| Mean2 | 5.0 | 4.8 | 87.7 | 94.3 | 96.0 | 94.4 | 77.7 |
| Locs | 13 | 25 | 2 | 6 | 5 | 17 | 49 |
| Reps | 13 | 25 | 2 | 6 | 5 | 17 | 49 |
| Diff | 1.5 | 0.5 | 5.3 | 1.2 | −2.0 | 2.1 | 12.3 |
| Prob | 0.002 | 0.058 | 0.411 | 0.697 | 0.374 | 0.352 | 0.001 |

FURTHER EMBODIMENTS OF THE INVENTION

This invention also is directed to methods for producing a maize plant by crossing a first parent maize plant with a second parent maize plant wherein either the first or second parent maize plant is Pioneer Brand hybrid 32A85. In one embodiment the parent hybrid maize plant 32A85 will be crossed with another maize plant, sibbed, or selfed, to generate an inbred which may be used in the development of additional plants. In another embodiment, double haploid methods may be used to generate an inbred plant. Further, this invention is directed to methods for producing a hybrid 32A85-progeny maize plant by crossing hybrid maize plant 32A85 with itself or a second maize plant and growing the progeny seed, and repeating the crossing and growing steps with the hybrid maize 32A85 progeny plant from 1 to 2 times, 1 to 3 times, 1 to 4 times, or 1 to 5 times. Thus, any such methods using the hybrid maize plant 32A85 are part of this invention: selfing, sibbing, backcrosses, hybrid production, crosses to populations, and the like.

All plants produced using hybrid maize plant 32A85 as a parent are within the scope of this invention, including plants derived from hybrid maize plant 32A85. This includes varieties essentially derived from variety 32A85 with the term essentially derived variety" having the meaning ascribed to such term in 7 U.S.C. § 2104(a)(3) of the Plant Variety Protection Act, which definition is hereby incorporated by reference. This also includes progeny plant and parts thereof with at least one ancestor that is hybrid maize plant 32A85 and more specifically where the pedigree of this progeny includes 1, 2, 3, 4, and/or 5 or cross pollinations to a maize plant 32A85, or a plant that has 32A85 as a progenitor. All breeders of ordinary skill in the art maintain pedigree records of their breeding programs. These pedigree records contain a detailed description of the breeding process, including a listing of all parental lines used in the breeding process and information on how such line was used. Thus, a breeder would know if 32A85 were used in the development of a progeny line, and would also know how many cross-pollinations to a line other than 32A85 were made in the development of any progeny line. A progeny line so developed may then be used in crosses with other, different, maize inbreds to produce first generation ($F_1$) maize hybrid seeds and plants with superior characteristics.

Specific methods and products produced using hybrid maize plant in plant breeding are encompassed within the scope of the invention listed above. One such embodiment is the method of crossing hybrid maize plant 32A85 with itself to form a homozygous inbred parent line. Hybrid 32A85 would be sib or self pollinated to form a population of progeny plants. The population of progeny plants produced by this method is also an embodiment of the invention. This first population of progeny plants will have received all of its alleles from hybrid maize plant 32A85. The inbreeding process results in homozygous loci being generated and is repeated until the plant is homozygous at substantially every loci and becomes an inbred line. Once this is accomplished the inbred line may be used in crosses with other inbred lines, including but not limited to inbred parent lines disclosed herein to generate a first generation of F1 hybrid plants. One of ordinary skill in the art can utilize breeder notebooks, or molecular methods to identify a particular hybrid plant produced using an inbred line derived from maize hybrid plant 32A85, in addition to comparing traits. Any such individual inbred plant is also encompassed by this invention.

These embodiments also include use of these methods with transgenic or single gene conversions of maize hybrid plant 32A85. Another such embodiment is a method of developing a line genetically similar to hybrid maize plant 32A85 in breeding that involves the repeated backcrossing of an inbred parent of, or an inbred line derived from, hybrid maize plant 32A85 to another different maize plant any number of times. Using backcrossing methods, or even the tissue culture and transgenic methods described herein, the single gene conversion methods described herein, or other breeding methods known to one of ordinary skill in the art, one can develop individual plants, plant cells, and populations of plants that retain at least 25%, 30%, 35%, 40%, 45%, 50%, 55%, 60%, 65%, 70%, 75% 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic similarity or identity to maize hybrid plant 32A85. The percentage of the genetics retained in the progeny may be measured by either pedigree analysis or through the use of genetic techniques such as molecular markers or electrophoresis. In pedigree analysis, on average 50% of the starting germplasm would be passed to the progeny line after one cross to a different line, 25% after another cross to a different line, and so on. Molecular markers could also be used to confirm and/or determine the pedigree of the progeny line. The inbred parent would then be crossed to a second inbred parent of or derived from hybrid maize plant 32A85 to create hybrid maize plant 32A85 with additional beneficial traits such as transgenes or single gene conversions.

One method for producing a line derived from hybrid maize plant is as follows. One of ordinary skill in the art would obtain hybrid maize plant 32A85 and cross it with another variety of maize, such as an elite inbred variety. The F1 seed derived from this cross would be grown to form a population. The nuclear genome of the F1 would be made-up of 50% of hybrid maize plant 32A85 and 50% of the other elite variety. The F1 seed would be grown and allowed to self, thereby forming F2 seed. On average the F2 seed nuclear genome would have derived 50% of its alleles from the parent hybrid plant 32A85 and 50% from the other maize variety, but various individual plants from the population would have a much greater percentage of their alleles derived from the parent maize hybrid plant (Wang J. and R. Bernardo, 2000, Crop Sci. 40: 659–665 and Bernardo, R. and A. L. Kahler, 2001, Theor. Appl. Genet 102: 986–992). Molecular markers of 32A85, or its parents identified from routine screening of the deposited samples herein could be used to select and retain those lines with high similarity to 32A85. The F2 seed would be grown and selection of plants would be made based on visual observation, markers and/or measurement of traits. The traits used for selection may be any 32A85 trait described in this specification, including the hybrid maize plant 32A85 traits of very good yield potential, excellent stalk lodging resistance, good plant health, good stay green, early growth, good grain quality, good food corn characteristics, good resistance to head smut, very good drought tolerance and particularly suited to the Central Corn Belt, Southcentral, Southwest, and Western regions of the United States.

Such traits may also be the good general or specific combining ability of 32A85, including its ability to produce single gene conversions, or other hybrids. The 32A85 progeny plants that exhibit one or more of the desired 32A85 traits, such as those listed above, would be selected and each plant would be harvested separately. This F3 seed from each plant would be grown in individual rows and allowed to self. Then selected rows or plants from the rows would be harvested individually. The selections would again be based on visual observation, markers and/or measurements for desirable traits of the plants, such as one or more of the desirable 32A85 traits listed above.

The process of growing and selection would be repeated any number of times until a 32A85 progeny plant is obtained. The 32A85 progeny inbred plant would contain desirable traits in hybrid combination derived from hybrid plant 32A85. The resulting progeny line would benefit from the efforts of the inventor(s), and would not have existed but for the inventor(s) work in creating 32A85. Another embodiment of the invention is a 32A85 progeny plant that has received the desirable 32A85 traits listed above through the use of 32A85, which traits were not exhibited by other plants used in the breeding process.

The previous example can be modified in numerous ways, for instance selection may or may not occur at every selfing generation, the hybrid may immediately be selfed without crossing to another plant, selection may occur before or after the actual self-pollination process occurs, or individual selections may be made by harvesting individual ears, plants, rows or plots at any point during the breeding process described. In addition, double haploid breeding methods may be used at any step in the process. The population of plants produced at each and any cycle of breeding is also an embodiment of the invention. In each case the use of 32A85 provides a substantial benefit. The linkage groups of 32A85 would be retained in the progeny lines, and since current estimates of the maize genome size is about 50,000–80,000 genes (Xiaowu, Gai et al., Nucleic Acids Research, 2000, Vol. 28, No. 1, 94–96), in addition to a large amount of non-coding DNA that impacts gene expression, it provides a significant advantage to use 32A85 as starting material to produce a line that retains desired genetics or traits of 32A85.

Another embodiment of this invention is the method of obtaining a substantially homozygous 32A85 progeny plant by obtaining a seed from the cross of 32A85 and another maize plant and applying double haploid methods to the F1 seed or F1 plant or to any successive filial generation. Such methods substantially decrease the number of generations required to produce an inbred with similar genetics or characteristics to 32A85.

A further embodiment of the invention is a single gene conversion of 32A85 obtained by crossing inbred parent plants of hybrid maize plant 32A85, which comprise the single gene conversion. For a dominant or additive trait at least one of the inbred parents would include single gene conversion in its genome. For a recessive trait, each parent would include the single gene conversion in its genome. In each case the resultant hybrid maize plant 32A85 obtained from the cross of the parents includes a single gene conversion or transgene. A single gene conversion occurs when DNA sequences are introduced through traditional (non-transformation) breeding techniques, such as backcrossing (Hallauer et al, 1988). DNA sequences, whether naturally occurring or transgenes, may be introduced using these traditional breeding techniques. The term single gene conversion is also referred to in the art as a single locus conversion. Reference is made to U.S. 2002/0062506A1 for a detailed discussion of single locus conversions and traits that may be incorporated into 32A85 through single gene conversion.

Desired traits transferred through this process include, but are not limited to, waxy starch, nutritional enhancements, industrial enhancements, disease resistance, insect resistance, herbicide resistance and yield enhancements. The trait of interest is transferred from the donor parent to the recurrent parent, in this case, an inbred parent of the maize plant disclosed herein. Single gene traits may result from either the transfer of a dominant allele or a recessive allele. Selection of progeny containing the trait of interest is done by direct selection for a trait associated with a dominant allele. Selection of progeny for a trait that is transferred via a recessive allele, such as the waxy starch characteristic, requires growing and selfing the first backcross to determine which plants carry the recessive alleles. Recessive traits may require additional progeny testing in successive backcross generations to determine the presence of the gene of interest. Along with selection for the trait of interest, progeny are selected for the phenotype of the recurrent parent. It should be understood that occasionally additional polynucleotide sequences or genes are transferred along with the single gene conversion trait of interest. A progeny comprising at least 98%, 99%, 99.5% and 99.9% genetic identity to the recurrent parent, the maize line disclosed herein, comprising the single gene conversion trait or traits of interest, is considered to be a single gene conversion of hybrid 32A85.

It should be understood that the plant can, through routine manipulation by detasseling, cytoplasmic genes, nuclear genes, or other factors, be produced in a male-sterile form. The term manipulated to be male sterile refers to the use of any available techniques to produce a male sterile version of maize line 32A85. The male sterility may be either partial or complete male sterility.

Such embodiments are also within the scope of the present claims. This invention includes hybrid maize seed of 32A85 and the hybrid maize plant produced therefrom. The foregoing was set forth by way of example and is not intended to limit the scope of the invention.

This invention is also directed to the use of hybrid maize plant 32A85 in tissue culture. As used herein, the terE plant includes plant protoplasts, plant cell tissue cultures from which maize plants can be regenerated, plant calli, plant clumps, and plant cells that are intact in plants, or parts of plants, such as embryos, pollen, ovules, flowers, kernels, ears, cobs, leaves, seeds, husks, stalks, roots, root tips, anthers, silk and the like. As used herein the phrase "growing the seed" or "grown from the seed" includes embryo rescue, isolation of cells from seed for use in tissue culture, as well as traditional growing methods.

Duncan, Williams, Zehr, and Widholm, *Planta*, (1985) 165: 322–332 reflects that 97% of the plants cultured which produced callus were capable of plant regeneration. Subsequent experiments with both inbreds and hybrids produced 91% regenerable callus which produced plants. In a further study in 1988, Songstad, Duncan & Widholm in Plant Cell Reports (1988), 7: 262–265 reports several media additions which enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter*, 60: 64–65 (1986), refers to somatic embryogenesis from glume callus cultures and B. V. Conger, et al., *Plant Cell Reports*, 6: 345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize is described in European Patent Application, publication 160,390, incorporated herein by reference. Maize tissue culture procedures are also described in Green and Rhodes, "Plant Regeneration in Tissue Culture of Maize," *Maize for Biological Research* (Plant Molecular Biology Association, Charlottesville, Va. 1982, at 367–372) and in Duncan, et al., "The Production of Callus Capable of Plant Regeneration from Immature Embryos of Numerous Zea Mays Genotypes," 165 *Planta* 322–332 (1985). Thus, another aspect of this invention is to provide cells which upon growth and differentiation produce maize plants having the genotype and/or physiological and morphological characteristics of hybrid maize plant 32A85.

The utility of hybrid maize plant 32A85 also extends to crosses with other species. Commonly, suitable species will be of the family Graminaceae, and especially of the genera *Zea, Tripsacum, Coix, Schlerachne, Polytoca, Chionachne*, and *Trilobachne*, of the tribe Maydeae. Potentially suitable for crosses with 32A85 may be the various varieties of grain sorghum, *Sorghum bicolor* (L.) Moench.

Transformation of Maize

The advent of new molecular biological techniques have allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequence, whether from a different species or from the same species, that are inserted into the genome using transformation are referred to herein collectively as "transgenes". Over the last fifteen to twenty years several methods for producing transgenic plants have been developed; and the present invention, in particular embodiments, also relates to transformed versions of the claimed hybrid maize plant 32A85.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc. Boca Raton, 1993) pages 67–88 and Armstrong, "The First Decade of Maize Transformation: A Review and Future Perspective" (Maydica 44: 101–109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89–119. See U.S. Pat. No. 6,118,055, which is herein incorporated by reference.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into a particular parent maize plant using transformation techniques, could be moved into another line using traditional breeding techniques that are well known in the plant breeding arts. These lines can then be crossed to generate a hybrid maize plant such as hybrid maize plant 32A85 which comprises a transgene. For example, a backcrossing approach could be used to move a transgene from a transformed maize plant to an elite inbred line and the resulting progeny would comprise a transgene. Also, if an inbred line was used for the transformation then the transgenic plants could be crossed to a different inbred in order to produce a transgenic hybrid maize plant. As used herein, "crossing" can refer to a simple X by Y cross, or the process of backcrossing, depending on the context.

Various genetic elements can be introduced into the plant genome using transformation. These elements include but are not limited to genes; coding sequences; inducible, constitutive, and tissue specific promoters; enhancing sequences; and signal and targeting sequences. See U.S. Pat. No. 6,284,953, which is herein incorporated by reference.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92–6 (1981).

According to a preferred embodiment, the transgenic plant provided for commercial production of foreign protein is maize. In another preferred embodiment, the biomass of interest is seed. A genetic map can be generated, primarily via conventional Restriction Fragment Length Polymorphisms (RFLP), Polymerase Chain Reaction (PCR) analysis, Simple Sequence Repeats (SSR) and Single Nucleotide Polymorphisms (SNP) which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269–284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, plants can be genetically engineered to express various phenotypes of agronomic interest. Through the transformation of maize the expression of genes can be modulated to enhance disease resistance, insect resistance, herbicide resistance, agronomic traits as well as grain quality traits. Transformation can also be used to insert DNA sequences which control or help control male-sterility. DNA sequences native to maize as well as non-native DNA sequences can be transformed into maize and used to modulate levels of native or non-native proteins. Anti-sense technology, various promoters, targeting sequences, enhancing sequences, and other DNA sequences can be inserted into the maize genome for the purpose of modulating the expression of proteins. Exemplary transgenes implicated in this regard include, but are not limited to, those categorized below.

1. Transgenes that Confer Resistance To Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266: 789 (1994) (cloning of the tomato Cf-9 gene for resistance to *Cladosporium fulvum*); Martin et al., *Science* 262: 1432 (1993) (tomato Pto gene for resistance to *Pseudomonas syringae* pv. tomato encodes a protein kinase); Mindrinos et al., *Cell* 78: 1089 (1994) (*Arabidopsis* RSP2 gene for resistance to *Pseudomonas syringae*).

(B) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt δ-endotoxin gene. Moreover, DNA molecules encoding δ-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and hereby are incorporated by reference: U.S. Pat. Nos. 5,188,960: 5,689,052; 5,880,275; and WO 97/40162.

(C) A lectin. See, for example, the disclosure by Van Damme et al., *Plant Molec. Biol.* 24: 25 (1994), who disclose the nucleotide sequences of several *Clivia miniata* mannose-binding lectin genes.

(D) A vitamin-binding protein such as avidin. See PCT application US93/06487 the contents of which are hereby incorporated by reference. The application teaches the use of avidin and avidin homologues as larvicides against insect pests.

(E) An enzyme inhibitor, for example, a protease inhibitor or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of cDNA encoding tobacco proteinase inhibitor I), and Sumitani et al., *Biosci. Biotech. Biochem.* 57: 1243 (1993) (nucleotide sequence of *Streptomyces nitrosporeus* α-amylase inhibitor) and U.S. Pat. No. 5,494,813.

(F) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(G) An insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific, paralytic neurotoxins.

(H) An insect-specific venom produced in nature by a snake, a wasp, etc. For example, see Pang et al., *Gene* 116: 165 (1992), for disclosure of heterologous expression in plants of a gene coding for a scorpion insectotoxic peptide.

(I) An enzyme responsible for an hyperaccumulation of a monterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene.

(K) A molecule that stimulates signal transduction. For example, see the disclosure by Botella et al, *Plant Molec.*

Biol. 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(L) A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

(M) A membrane permease, a channel former or a channel blocker. For example, see the disclosure by Jaynes et al., *Plant Sci.* 89: 43 (1993), of heterologous expression of a cecropin-β lytic peptide analog to render transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(O) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(P) A virus-specific antibody. See, for example, Tavladoraki et al., *Nature* 366: 469 (1993), who show that transgenic plants expressing recombinant antibody genes are protected from virus attack.

(O) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(R) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(S) Genes involved in the Systemic Acquired Resistance (SAR) Response and/or the pathogenesis related genes. Briggs, S., Current Biology, 5(2) (1995).

(T) Antifungal genes (Cornelissen and Melchers, Pl. Physiol. 101: 709–712, (1993) and Parijs et al., Planta 183: 258–264, (1991) and Bushnell et al., Can. J. of Plant Path. 20(2): 137–149 (1998).

2. Transgenes that Confer Resistance to a Herbicide, for Example:

(A) A herbicide that inhibits the growing point or meristem, such as an imidazalinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference in their entireties for all purposes.

(B) Glyphosate (resistance imparted by mutant 5-enolpyruvl-3-phosphikimate synthase (EPSP), and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and U.S. Pat. No. 5,491,288; and international publications WO 97/04103; WO 97/04114; WO 00/66746; WO 01/66704; WO 00/66747 and WO 00/66748, which are incorporated herein by reference in their entirety. Glyphosate resistance is also imparted to plants that express a gene that encodes a glyphosate oxido-reductase enzyme as described more fully in U.S. Pat. Nos. 5,776,760 and 5,463,175, which are incorporated herein by reference in their entirety. In addition glyphosate resistance can be imparted to plants by the over expression of genes encoding glyphosate N-acetyltransferase. See, for example, U.S. Application Ser. Nos. 60/244,385; 60/377,175 and 60/377,719.

A DNA molecule encoding a mutant aroA gene can be obtained under ATCC Accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European patent No. 0 242 246 and 0 242 236 to Leemans et al. De Greef et al., *Bio/Technology* 7: 61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference in their entirety. Exemplary of genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+genes) and a benzonitrile (nitrilase gene). Przibilla et al., *Plant Cell* 3: 169 (1991), describe the transformation of *Chlamydomonas* with plasmids encoding mutant psbA' genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

(D) Acetohydroxy acid synthase, which has been found to make plants that express this enzyme resistant to multiple types of herbicides, has been introduced into a variety of plants (see, e.g., Hattori et al. (1995) Mol Gen Genet 246:

419). Other genes that confer tolerance to herbicides include: a gene encoding a chimeric protein of rat cytochrome P4507A1 and yeast NADPH-cytochrome P450 oxidoreductase (Shiota et al. (1994) Plant Physiol Plant Physiol 106: 17), genes for glutathione reductase and superoxide dismutase (Aono et al. (1995) Plant Cell Physiol 36: 1687, and genes for various phosphotransferases (Datta et al. (1992) Plant Mol Biol 20: 619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825, which are incorporated herein by reference in their entireties of all purposes.

3. Transgenes that Confer or Contribute to a Value-added Trait, Such As:

(A) Modified fatty acid metabolism, for example, by transforming a plant with an antisense gene of stearoyl-ACP desaturase to increase stearic acid content of the plant. See Knultzon et al., *Proc. Natl. Acad. Sci. USA* 89: 2624 (1992).

(B) Decreased phytate content
  (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.
  (2) A gene could be introduced that reduces phytate content. In maize, this, for example, could be accomplished, by cloning and then re-introducing DNA associated with the single allele which is responsible for maize mutants characterized by low levels of phytic acid. See Raboy et al., *Maydica* 35: 383 (1990).

(C) Modified carbohydrate composition effected, for example, by transforming plants with a gene coding for an enzyme that alters the branching pattern of starch. See Shiroza et al., *J. Bacteriol.* 170: 810 (1988) (nucleotide sequence of *Streptococcus mutans* fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis* α-amylase), Elliot et at., *Plant Molec. Biol.* 21: 515 (1993) (nucleotide sequences of tomato invertase genes), Søgaard et al., *J. Biol. Chem.* 268: 22480 (1993) (site-directed mutagenesis of barley α-amylase gene), and Fisher et al., *Plant Physiol.* 102: 1045 (1993) (maize endosperm starch branching enzyme II).

(D) Elevated oleic acid via FAD-2 gene modification and/or decreased linolenic acid via FAD-3 gene modification (see U.S. Pat. Nos. 6,063,947; 6,323,392; and WO 93/11245).

4. Genes that Control Male-sterility
  (A) Introduction of a deacetylase gene under the control of a tapetum-specific promoter and with the application of the chemical N-Ac-PPT (WO 01/29237).
  (B) Introduction of various stamen-specific promoters (WO 92/13956, WO 92/13957).
  (C) Introduction of the barnase and the barstar gene (Paul et al. Plant Mol. Biol. 19: 611–622, 1992).

Genetic Marker Profile Through SSR

The present invention comprises a hybrid corn plant which is characterized by the molecular and physiological data presented herein and in the representative sample of said hybrid and of the inbred parents of said hybrid deposited with the ATCC.

As discussed, supra, in addition to phenotypic observations, a plant can also be described by its genotype. The genotype of a plant can be described through a genetic marker profile which can identify plants of the same variety, a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Berry, Don, et al., "Assessing Probability of Ancestry Using Simple Sequence Repeat Profiles: Applications to Maize Hybrids and Inbreds", Genetics, 2002, 161: 813–824, which is incorporated by reference herein in its entirety.

Particular markers used for these purposes are not limited to the set of markers disclosed herewithin, but are envisioned to include any type of marker and marker profile which provides a means of distinguishing varieties. In addition to being used for identification of inbred parents, hybrid variety 32A85, a hybrid produced through the use of 32A85 or its parents, and the identification or verification of pedigree for progeny plants produced through the use of 32A85, the genetic marker profile is also useful in breeding and developing single gene conversions.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR™ detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by gel electrophoresis of the amplification products. Scoring of marker genotype is based on the size of the amplified fragment as measured by molecular weight (MW) rounded to the nearest integer. While variation in the primer used or in laboratory procedures can affect the reported molecular weight, relative values should remain constant regardless of the specific primer or laboratory used. When comparing lines it is preferable if all SSR profiles are performed in the same lab. An SSR service is available to the public on a contractual basis by Paragen, research Trianbgle Park, N.C., (formerly Celera AgGen of Davis, Calif.

Primers used for the SSRs suggested herein are publicly available and may be found in the Maize DB using the World Wide Web prefix agron.missouri.edu (sponsored by the University of Missouri), in Sharopova et al. (Plant Mol. Biol. 48(5–6): 463–481), Lee et al. (Plant Mol. Biol. 48(5–6): 453–461). Some marker information may be available from Paragen.

Map information is provided in centimorgans (cM) and based on a composite map developed by Pioneer Hi-Bred. This composite map was created by identifying common markers between various maps and using linear regression to place the intermediate markers. The reference map used was UMC98. Map positions for the SSR markers reported herein will vary depending on the mapping population used. Any chromosome numbers reported in parenthesis represent other chromosome locations for such marker that have been reported in the literature or on the Maize DB. Map positions are available on the Maize DB for a variety of different mapping populations.

TABLE A

| Locus | Chrom # | Position |
|---|---|---|
| PHI056 | 1 | 4.25 |
| PHI427913 | 1 | 26.71 |
| BNLG1014 | 1 | 29.8 |
| BNLG1429 | 1 | 30.68 |
| BNLG1627 | 1 | 34.03 |
| BNLG1127 | 1 | 38.07 |
| BNLG1953 | 1 | 38.34 |
| BNLG1484 | 1 | 53.32 |
| BNLG439 | 1 | 62.42 |
| BNLG1203 | 1 | 62.42 |
| PHI339017 | 1 | 70.05 |
| BNLG2238 | 1 | 77.52 |
| BNLG1886 | 1 | 91.64 |
| BNLG2086 | 1 | 94.5 |
| BNLG1057 | 1 | 142.56 |
| BNLG1615 | 1 | 142.74 |
| BNLG1556 | 1 | 150.53 |
| PHI002 | 1 | 168.21 |
| PHI423298 | 1 | 174.38 |
| PHI323065 | 1 | 177.39 |
| PH1335539 | 1 | 178.84 |
| PHI011 | 1 | 190.09 |
| BNLG1331 | 1 | 193.48 |
| BNLG1597 | 1 | 199.42 |
| BNLG1720 | 1 | 199.44 |
| PHI308707 | 1 | 211.59 |
| PHI265454 | 1 | 221.46 |
| PHI227562 | 1 | 242.7 |
| PHI064 | 1 | 243.08 |
| PHI109275 | 1 | unknown |
| BNLG1832 | 1 | unknown |
| BNLG1083 | 1 | unknown |

TABLE A-continued

| Locus | Chrom # | Position |
|---|---|---|
| BNLGL1016 | 1 | unknown |
| PHI961000 | 2 | 6.99 |
| BNLG1017 | 2 | 21.79 |
| BNLG2277 | 2 | 55.07 |
| BNLG1064 | 2 | 64.21 |
| PHI109642 | 2 | 69.93 |
| BNLG1909 | 2 | 76.87 |
| BNLG1018 | 2 | 77.92 |
| BNLG1396 | 2 | 120.07 |
| BNLG1138 | 2 | 121.18 |
| PHI328189 | 2 | 145.57 |
| BNLG2237 | 2 | 148.65 |
| PHI251315 | 2 | 149.77 |
| PHI127 | 2 | 152.84 |
| PHI101049 | 2 | 207.93 |
| BNLG1940 | 2 | 270.85 |
| PHI435417 | 2 | 302.56 |
| BNLG1520 | 2 | 375.32 |
| PHI427434 | 2 | 413.55 |
| PHI402893 | 2 | unknown |
| PHI090 | 2 | unknown |
| PHI083 | 2 | unknown |
| BNLG1831 | 2 | unknown |
| BNLG1141 | 2 | unknown |
| PH1453121 | 3 | 0.2 |
| PHI404206 | 3 | 2.2 |
| PHI104127 | 3 | 5.68 |
| BNLG1144 | 3 | 23.52 |
| BNLG1647 | 3 | 33.98 |
| BNLG1523 | 3 | 34.3 |
| PHI243966 | 3 | 52.24 |
| PHI374118 | 3 | 53.66 |
| BNLG1452 | 3 | 58.58 |
| BNLG1113 | 3 | 58.65 |
| BNLG1019 | 3 | 58.65 |
| PHI053 | 3 | 67.9 |
| PHI102228 | 3 | 104.98 |
| BNLG1951 | 3 | 108.98 |
| BNLG1160 | 3 | 110.2 |
| PHI1932 | 3 | 159.24 |

TABLE A-continued

SSR Markers

| Locus | Chrom # | Position |
|---|---|---|
| PHI07325 | 3 | unknown |
| PHI029 | 3 | unknown |
| BNLG2241 | 3 | unknown |
| BNLG1035 | 3 | unknown |
| PHI295450 | 4 | 16.87 |
| PHI213984 | 4 | 25.02 |
| BNLG1162 | 4 | 40.01 |
| PHI096 | 4 | 61.84 |
| PHI079 | 4 | 65.46 |
| BNLG1937 | 4 | 65.49 |
| BNLG1265 | 4 | 67.31 |
| BNLG1755 | 4 | 91.45 |
| BNLG1189 | 4 | 108.12 |
| BNLG2244 | 4 | 122.51 |
| PHI093 | 4 | 126.18 |
| PHI314704 | 4 | 159.67 |
| PHI438301 | 4 | 819.88 |
| PHI308090 | 4 | unknown |
| PHI076 | 4 | unknown |
| PHI072 | 4 | unknown |
| BNLG1006 | 5 | 15.9 |
| PHI396160 | 5 | 76.45 |
| PHI109188 | 5 | 77.97 |
| BNLG653 | 5 | 88.43 |
| PHI331888 | 5 | 91.48 |
| BNLG1208 | 5 | 94.95 |
| PHI386223 | 5 | 95.46 |
| BNLG1892 | 5 | 97.9 |
| PHI330507 | 5 | 102.23 |
| PHI333597 | 5 | 103.48 |
| PHI196387 | 5 | 133.31 |
| PHI085 | 5 | 136.05 |
| BNLG1118 | 5 | 149.53 |
| BNLG1711 | 5 | 178.37 |
| PHI159819 | 6 | 22.8 |
| PHI423796 | 6 | 31.29 |
| PHI389203 | 6 | 83.56 |
| PHI452693 | 6 | 98.06 |
| BNLG1041 | 6 | 98.1 |
| BNLG1174 | 6 | 99.41 |
| PHI445613 | 6 | 106.74 |
| PHI364545 | 6 | 126.24 |
| PHI299852 | 6 | 129.9 |
| PHI070 | 6 | 129.9 |
| BNLG1759 | 6 | 129.9 |
| BNLG1740 | 6 | 129.9 |
| PHI034 | 7 | 54.75 |
| BNLG2271 | 7 | 95.38 |
| PHI328175 | 7 | 100.36 |
| PHI260485 | 7 | 134.62 |
| PHI069 | 7 | 137.5 |
| PHI051 | 7 | 137.5 |
| PHI116 | 7 | 149.22 |
| PHI420701 | 8 | 24.32 |
| BNLG1194 | 8 | 27.24 |
| BNLG2082 | 8 | 55.3 |
| PHI100175 | 8 | 60.43 |
| PHI115 | 8 | 64.03 |
| PHI121 | 8 | 66.43 |
| BNLG2046 | 8 | 75.05 |
| BNLG1176 | 8 | 79.72 |
| BNLG1152 | 8 | 111.61 |
| BNLG1065 | 8 | 127.89 |
| BNLG1056 | 8 | 193.84 |
| PHI015 | 8 | 210.92 |
| PHI233376 | 8 | 219.36 |
| BNLG2122 | 9 | 32.11 |
| BNLG1012 | 9 | 84.23 |
| PHI032 | 9 | 86.67 |
| BNLG619 | 9 | 122.79 |
| PHI448880 | 9 | 126.07 |
| PHI236654 | 9 | 157.45 |
| PHI108411 | 9 | 169.83 |
| PHI033 | 9 | unknown |
| BNLG1375 | 9 | unknown |
| BNLG1129 | 9 | unknown |
| PHI041 | 10 | 9.6 |
| PHI059 | 10 | 40.55 |
| PHI96342 | 10 | 52.8 |
| BNLG1079 | 10 | 62.12 |
| PHI050 | 10 | 63 |
| PHI062 | 10 | 69.31 |
| BNLG1074 | 10 | 85.74 |
| PHI301654 | 10 | 91.26 |
| PHI323152 | 10 | 117.1 |
| BNLG14 | 10 | 126.36 |

TABLE A-continued

SSR Markers

| Locus | Chrom # | Position |
|---|---|---|
| 50 BNLG1185 | 10 | 142.38 |
| BNLG1597 | 5 (1, 6) | 154.8 |

A genetic marker profile of a hybrid should be the sum of its inbred parents, e.g., if one inbred parent had the allele 168 (base pairs) at a particular locus, and the other inbred parent had 172 the hybrid is 168.172 (heterozygous) by inference. Subsequent generations of progeny produced by selection and breeding are expected to be of genotype 168 (homozygous), 172 (homozygous), or 168.172 for that locus position. When the F1 plant is used to produce an inbred, the locus should be either 168 or 172 for that position.

In addition, plants and plant parts substantially benefiting from the use of 32A85 in their development such as 32A85 comprising a single gene conversion, transgene, or genetic sterility factor, may be identified by having a molecular marker profile with a high percent identity to 32A85. Such a percent identity might be 98%, 99%, 99.5% or 99.9% identical to 32A85.

The SSR profile of 32A85 also can be used to identify essentially derived varieties and other progeny lines developed from the use of 32A85, as well as cells and other plant parts thereof. Progeny plants and plant parts produced using 32A85 may be identified by having a molecular marker profile of at least 25%, 30%, 35%, 40%, 45%, 50%, 55%, 60%, 65%, 70%, 75%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from hybrid maize plant 32A85.

INDUSTRIAL APPLICABILITY

Maize is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize are also used in industry: for example, stalks and husks are made into paper and wallboard and cobs are used for fuel and to make charcoal.

The seed of the hybrid maize plant, the plant produced from the seed, a plant produced from crossing of maize hybrid plant 32A85 and various parts of the hybrid maize plant and transgenic versions of the foregoing, can be utilized for human food, livestock feed, and as a raw material in industry.

DEPOSITS

Applicant has made a deposit of at least 2500 seeds of hybrid maize plant 32A85 and inbred parent plants GE515488 and GE587272 with the American Type Culture Collection (ATCC). Manassas, Va. 20110 USA, ATCC Deposit Nos. PTA-5488, PTA-1304, and PTA-5532 respectively. The seeds deposited with the ATCC on Sep. 11, 2003, Feb. 4, 2000, and Sep. 15, 2003 respectively were taken from the deposit maintained by Pioneer Hi-Bred International, Inc., 800 Capital Square, 400 Locust Street, Des Moines, Iowa 50309-2340, since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant(s) will make available to the public, pursuant to 37 C.F.R. § 1.808, a deposit of at least 2500 seeds of hybrid maize plant 32A85 and inbred parent plants GE515488 and GE587272 with the American Type Culture Collection (ATCC), 10801 University Boulevard, Manassas, Va. 20110-2209. This deposit of seed of hybrid maize plant 32A85 and inbred parent plants GE515488 and GE587272 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant(s) will meet all the requirements of 37 C.F.R. §§1.801–1.809, including providing an indication of the viability of the sample upon deposit. Applicant has no authority to waive any restrictions imposed by law on the transfer of biological material or its transportation in commerce. Applicant does not waive any infringement of its rights granted under this patent or under the Plant Variety Protection Act (7 USC 2321 et seq.).

All publications, patents and patent applications mentioned in the specification are indicative of the level of those skilled in the art to which this invention pertains. All such publications, patents and patent applications are incorporated by reference herein to the same extent as if each was specifically and individually indicated to be incorporated by reference herein.

The foregoing invention has been described in detail by way of illustration and example for purposes of clarity and understanding. However, it will be obvious that certain changes, and modifications such as single gene conversions and mutations, somoclonal variants, variant individuals selected from large populations of the plants of the instant inbred and the like may be practiced within the scope of the invention, as limited only by the scope of the appended claims.

What is claimed is:

1. Seed of hybrid maize variety designated 32A85, representative seed of said variety having been deposited under ATCC Accession No. PTA-5488.

2. A maize plant, or a part thereof, produced by growing the seed of claim 1.

3. Pollen of the plant of claim 2.

4. An ovule of the plant of claim 2.

5. A tissue culture of regenerable cells produced from the plant of claim 2.

6. Protoplasts produced from the tissue culture of claim 5.

7. The tissue culture of claim 5, wherein cells of the tissue culture are from a tissue selected from the group consisting of leaf, pollen, embryo, root, root tip, anther, silk, flower, kernel, ear, cob, husk and stalk.

8. A maize plant regenerated from the tissue culture of claim 5, said plant having all the morphological and physiological characteristics of hybrid maize plant 32A85, representative seed of said plant having been deposited under ATCC Accession No. PTA-5488.

9. A method for producing an F1 hybrid maize seed, comprising crossing the plant of claim 2 with a different maize plant and harvesting the resultant F1 hybrid maize seed.

10. A maize plant, or a part thereof, having all the physiological and morphological characteristics of the hybrid maize plant 32A85, representative seed of said plant having been deposited under ATCC Accession No.PTA-5489.

11. A method of introducing a desired trait into a hybrid maize variety 32A85 comprising:
(a) crossing at least one of inbred maize parent plants GE515488 and GE587272, representative samples of which have been deposited under ATCC Accession Nos. as PTA-1304 and PTA-5532 respectively, with another maize line that comprises a desired trait, to produce F1 progeny plants, wherein the desired trait is selected from the group consisting of male sterility, herbicide resistance, insect resistance, disease resistance and waxy starch;
(b) selecting said F1 progeny plants that have the desired trait to produce selected F1 progeny plants;
(c) backcrossing the selected progeny plants with said inbred maize parent plant to produce backcross progeny plants;
(d) selecting for backcross progeny plants that have the desired trait and morphological and physiological characteristics of said inbred maize parent plant;
(e) repeating steps (c) and (d) three or more times in succession to produce selected fourth or higher backcross progeny plants;
(f) crossing said fourth or higher backcross progeny plant with the other inbred maize parent plant to generate a hybrid maize variety 32A85 with the desired trait and all of the morphological and physiological characteristics of hybrid maize variety 32A85 listed in Table 1 as determined at the 5% significance level when grown in the same environmental conditions.

12. A plant produced by the method of claim 11, wherein the plant has the desired trait and all of the physiological and morphological characteristics of hybrid maize variety 32A85 listed in Table 1 as determined at the 5% significance level when grown in the same environmental conditions.

13. The plant of claim 12 wherein the desired trait is herbicide resistance and the resistance is conferred to an herbicide selected from the group consisting of: imidazolinone, sulfonylurea, glyphosate, glufosinate, L-phosphinothricin, triazine and benzonitrile.

14. The plant of claim 12 wherein the desired trait is insect resistance and the insect resistance is conferred by a transgene encoding a *Bacillus thuringiensis* endotoxin.

15. The plant of claim 12 wherein the desired trait is male sterility and the trait is conferred by a cytoplasmic nucleic acid molecule that confers male sterility.

16. A method of modifying fatty acid metabolism, phytic acid metabolism or carbohydrate metabolism in a hybrid maize variety 32A85 comprising:
(a) crossing at least one of inbred maize parent plants GE515488 and GE587272, representative samples of which have been deposited under ATCC Accession Nos. as PTA-1304 and PTA-5532 respectively, with another maize line that comprise a nucleic acid molecule encoding an enzyme selected from the group consisting of phytase, stearoyl-ACP desaturase, fructosyltransferase, levansucrase, alpha-amylase, invertase and starch branching enzyme;
(b) selecting said F1 progeny plants that have said nucleic acid molecule to produce selected F1 progeny plants;
(c) backcrossing the selected progeny plants with said inbred maize parent plant to produce backcross progeny plants;
(d) selecting for backcross progeny plants that have said nucleic acid molecule and morphological and physiological characteristics of said inbred maize parent plant;
(e) repeating steps (c) and (d) three or more times in succession to produce selected fourth or higher backcross progeny plants;
(f) crossing said fourth or higher backcross progeny plant with the other inbred maize parent plant to generate a hybrid maize variety 32A85 that comprises said nucleic acid molecule and has all of the morphological and physiological characteristics of hybrid maize variety 32A85 listed in Table 1 as determined at the 5% significance level when grown in the same environmental conditions.

17. A plant produced by the method of claim 16, wherein the plant comprises the nucleic acid molecule and has all of the physiological and morphological characteristics of hybrid maize variety 32A85 listed in Table 1 as determined at the 5% significance level when grown in the same environmental conditions.

18. A method for producing a maize seed, comprising crossing the plant of claim 2 with itself or a different maize plant and harvesting the resultant maize seed.

* * * * *